(12) United States Patent
Shoshan-Barmatz

(10) Patent No.: US 9,758,559 B2
(45) Date of Patent: Sep. 12, 2017

(54) SHORT PEPTIDES DERIVED FROM VDAC1, COMPOSITIONS AND METHODS OF USE THEREOF

(71) Applicants: B.G. NEGEV TECHNOLOGIES AND APPLICATIONS LTD., AT BEN-GURION UNIVERSITY, Beer-Sheva (IL); THE NATIONAL INSTITUTE FOR BIOTECHNOLOGY IN THE NEGEV LTD., Beer-Sheva (IL)

(72) Inventor: Varda Shoshan-Barmatz, Omer (IL)

(73) Assignees: B.G. Negev Technologies and Applications Ltd., at Ben-Gurion University, Beer-Sheva (IL); The National Institute for Biotechnology in the Negev Ltd., Beer-Sheva (IL)

(*) Notice: Subject to any disclaimer, the term of this patent is extended or adjusted under 35 U.S.C. 154(b) by 102 days.

(21) Appl. No.: 14/907,445

(22) PCT Filed: Jul. 24, 2014

(86) PCT No.: PCT/IL2014/050675
§ 371 (c)(1),
(2) Date: Jan. 25, 2016

(87) PCT Pub. No.: WO2015/011711
PCT Pub. Date: Jan. 29, 2015

(65) Prior Publication Data
US 2016/0176937 A1  Jun. 23, 2016

Related U.S. Application Data

(60) Provisional application No. 61/858,125, filed on Jul. 25, 2013.

(51) Int. Cl.
C07K 14/435 (2006.01)
C07K 14/47 (2006.01)
(Continued)

(52) U.S. Cl.
CPC .... *C07K 14/4747* (2013.01); *A61K 47/48315* (2013.01); *C07K 14/43581* (2013.01); *A61K 38/00* (2013.01); *C07K 2319/00* (2013.01)

(58) Field of Classification Search
CPC .............. A61K 38/00; A61K 47/48315; C07K 14/43581; C07K 14/4747; C07K 2319/00
See application file for complete search history.

(56) References Cited

U.S. PATENT DOCUMENTS

| 5,288,707 A | 2/1994 | Metternich |
| 5,391,377 A | 2/1995 | Barnwell |

(Continued)

FOREIGN PATENT DOCUMENTS

| WO | 02/083712 | 10/2002 |
| WO | 03/031650 | 4/2003 |

(Continued)

OTHER PUBLICATIONS

Abu-Hamad et al., (2009) The VDAC1 N-terminus is essential both for apoptosis and the protective effect of anti-apoptotic proteins. J Cell Sci 122(Pt 11): 1906-16.
(Continued)

*Primary Examiner* — Randall L Beane
(74) *Attorney, Agent, or Firm* — Winston & Strawn LLP

(57) ABSTRACT

The present invention relates to short peptides based on the amino acids sequence of the N-terminal domain of the human mitochondrial protein voltage-dependent anion channel 1 (VDAC) and to peptide conjugates having a cell permeability enhancing moiety. The peptides, peptide conjugates and pharmaceutical compositions containing them
(Continued)

are useful for treating diseases characterized by cell hyperproliferation or resistance to cell death and in particular, cancer.

8 Claims, 6 Drawing Sheets

(51) Int. Cl.
    *A61K 47/48*     (2006.01)
    *A61K 38/00*     (2006.01)

(56) References Cited

U.S. PATENT DOCUMENTS

| | | |
|---|---|---|
| 5,550,251 A | 8/1996 | Hirschmann |
| 5,552,534 A | 9/1996 | Hirschmann |
| 5,780,235 A | 7/1998 | Bandman |
| 5,811,392 A | 9/1998 | Gilon |
| 5,910,478 A | 6/1999 | Hlavka |
| 5,965,539 A | 10/1999 | Sebti |
| 6,165,732 A | 12/2000 | Korsmeyer |
| 6,291,247 B1 | 9/2001 | Riopelle |
| 8,119,601 B2 | 2/2012 | Shoshan-Barmatz |
| 8,440,788 B2 | 5/2013 | Shoshan-Barmatz |
| 8,648,045 B2 | 2/2014 | Shoshan-Barmatz |
| 2004/0096444 A1 | 5/2004 | Pizzo |
| 2005/0085420 A1 | 4/2005 | Korsmeyer |
| 2005/0234116 A1 | 10/2005 | Sugiyama |
| 2008/0274962 A1* | 11/2008 | Shoshan-Barmatz C07K 14/4747 514/12.2 |
| 2012/0214741 A1 | 8/2012 | Shoshan-Barmatz |

FOREIGN PATENT DOCUMENTS

| | | |
|---|---|---|
| WO | 2004/016230 | 2/2004 |
| WO | 2007/113837 | 10/2007 |

OTHER PUBLICATIONS

Arbel and Shoshan-Barrnatz (2010) Voltage-dependent anion channel 1-based peptides interact with Bcl-2 to prevent antiapoptotic activity. J Biol Chem 285(9): 6053-62.
Arbel et al., (2012) Mediation of the antiapoptotic activity of Bcl-xL protein upon interaction with VDAC1 protein. J Biol Chem 287(27): 23152-61.
Arzoine et al., (2009) Voltage-dependent anion channel 1-based peptides interact with hexokinase to prevent its anti-apoptotic activity. J Biol Chem 284(6): 3946-55.
Azoulay-Zohar et al., (2004) In self-defence: hexokinase promotes voltage-dependent anion channel closure and prevents mitochondria-mediated apoptotic cell death. Biochem J 377(Pt 2): 347-55.
Blachly-Dyson et al., (1993) Cloning and functional expression in yeast of two human isoforms of the outer mitochondrial membrane channel, the voltage-dependent anion channel. J Biol Chem 268(3): 1835-41.
Bourgeron et al., (1992) Isolation and characterization of mitochondria from human B lymprioblastoid cell lines. Biochem Biophys Res Commun 186(1): 16-23.
Cochran et al., (2001) Tryptophan zippers: stable, monomeric beta-hairpins. Proc Natl Acad Sci U S A 98(10): 5578-83 and corrections.
Colonbini (2004) VDAC: The channel at the interface beween mitochondria and the cytosol. Molecular and Cellular Biochemistry 256(1): 107-115.
Geula et al., (2012) Structure-based analysis of VDAC1: N-terminus location, translocation, channel gating and association with anti-apoptotic proteins. Biochem J 444(3): 475-85.
Godbole et al., (2003) VDAC is a conserved element of death pathways in plant and animal systems. Biochim Biophys Acta 1642(1-2): 87-96.

Järver and Langel (2004) The use of cell-penetrating peptides as a tool for gene regulation. Drug Discov Today 9(9): 395-402.
Kim (2005) Unknotting the roles of Bcl-2 and Bcl-xL in cell death. Biochem Biophys Res Commun 333(2): 336-43.
Kitada et al., (1998) Expression of apoptosis-regulating proteins in chronic lymphocytic leukemia: correlations with In vitro and In vivo chemoresponses. Blood 91(9): 3379-89.
Lawen et al., (2005) Voltage-dependent anion-selective channel 1 (VDAC1)—a mitochondrial protein, rediscovered as a novel enzyme in the plasma membrane. Int J Biochem Cell Biol 37(2): 277-82.
Lazar et al., (1988) Transforming growth factor alpha: mutation of aspartic acid 47 and leucine 48 results in different biological activities. Mol Cell Biol 8(3): 1247-52.
Li et al., (2004) A small molecule Smac mimic potentiates TRAIL- and TNFalpha-mediated cell death. Science 305 (5689): 1471-4.
Mendoza et al., (2005) Anti-tumor chemotherapy utilizing peptide-based approaches—apoptotic pathways, kinases, and proteasome as targets. Arch Immunol Ther Exp (Warsz) 53(1): 47-60.
Messina et al., (2000) Characterization of the human porin isoform 1 (HVDAC1) gene by amplification on the whole human genome: A tool for porin deficiency analysis. Biochem Biophys Res Commun 270(3): 787-92.
Montserrat and Moreno (2008) Chronic lymphocytic leukaemia: a short overview. Ann Oncol 19 Suppl 7: vii320-5.
Oupický et al., (2002) Development of long-circulating polyelectrolyte complexes for systemic delivery of genes. J Drug Target 10(2): 93-8.
Pillai and Panchagnula (2001) Polymers in drug delivery. Curr Opin Chem Biol 5(4): 447-51.
Prezrna et al., (2013) VDAC1-based peptides: novel pro-apoptotic agents and potential therapeutics for B-cell chronic lymphocytic leukemia. Cell Death Dis 4: e809; 11 pages.
Rostovtseva et al., (2005) On the role of VDAC in apoptosis: fact and fiction. J Bioenerg Biomembr 37(3): 129-42.
Sapra and Alien (2004) Improved outcome when B-cell lymphoma is treated with combinations of immunoliposomal anticancer drugs targeted to both the CD19 and CD20 epitopes. Clin Cancer Res 10(7): 2530-7.
Schatzlein (2003) Targeting of Synthetic Gene Delivery Systems. J Biomed Biotechnol 2003(2): 149-158.
Shi et al., (2003) Identification of the protein-protein contact site and interaction mode of human VDAC1 with Bcl-2 family proteins. Biochem Biophys Res Commun 305(4): 989-96.
Shimizu et al., (1999) Bcl-2 family proteins regulate the release of apoptogenic cytochrome c by the mitochondrial channel VDAC. Nature 399(6735): 483-7.
Shimizu et al., (2001) Essential role of voltage-dependent anion channel in various forms of apoptosis in mammalian cells. J Cell Biol 152(2): 237-50.
Shoshan-Barmatz and Ben-Hail (2012) VDAC, a multi-functional mitochondrial protein as a pharmacological target. Mitochondrion 12(1): 24-34.
Shoshan-Barmatz and Gincel (2003) The voltage-dependent anion channel: characterization, modulation, and role in mitochondrial function in cell life and death. Cell Biochem Biophys 39(3): 279-92.
Shoshan-Barmatz and Golan (2012) Mitochondrial VDAC1: function in cell life and death and a target for cancer therapy. Curr Med Chem 19(5): 714-35.
Shoshan-Barmaz et al., (2010) VDAC, a multi-functional mitochondrial protein regulating cell life and death. Mol Aspects Med 31(3): 227-85.
Sugiyama et al., (2002) Activation of mitrochondrial voltage-dependent anion channel by apro-apoptotic BH3-only protein Bim. Oncogene 21(32): 4944-56.
Tracy (1998) Development and scale-up of a microsphere protein delivery system. Biotechnol Prog 14(1): 108-15.
Tsujimoto and Shimizu (2002) The voltage-dependent anion channel: an essential player in apoptosis. Biochimie 84(2-3): 187-93.
Wagner et al., (2005) Targeting of polyplexes: toward synthetic virus vector systems. Adv Genet 53: 333-54.
Walensky et al., (2004) Activation of apoptosis in vivo by a hydrocarbon-stapled BH3 helix. Science 305(5689): 1466-70.

(56) References Cited

OTHER PUBLICATIONS

Wells (1990) Additivity of mutational effects in proteins. Biochemistry 29(37): 8509-8517.
Zabala et al., (2004) Optimization of the Tet-on system to regulate interleukin 12 expression in the liver for the treatment of hepatic tumors. Cancer Res 64(8): 2799-804.
Zaid et al., (2005) The voltage-dependent anion channel-1 modulates apoptotic cell death. Cell Death Differ 12(7): 751-60.
Zalk et al., (2005) Oligomeric states of the voltage-dependent anion channel and cytochrome c release from mitochondria. Biochem J 386(Pt 1): 73-83.
Zheng et al., (2004) Essential role of the voltage-dependent anion channel (VDAC) in mitochondrial permeability transition pore opening and cytochrome c release induced by arsenic trioxide. Oncoaene 23(6): 1239-47.
Accession No. P45879 or Q3ZCK0 or Q71SW7, Nov. 1, 1995; 9 pages.
Kayser H. et al Database UniProt; May 1, 1991 XP002395032.
Accession No. vdaci_human, Database accession No. P21796, Q5FVE7, Q9UIQ5, Q9UPL0: 5 pages.

\* cited by examiner

Control

D-Δ(1-14) N-Ter-Antp

SHORT PEPTIDES DERIVED FROM VDAC1, COMPOSITIONS AND METHODS OF USE THEREOF

This application is a 371 filing of International Patent Application PCT/IL2014/050675 filed Jul. 24, 2014, which claims the benefit of application No. 61/858,125 filed Jul. 5, 2013.

FIELD OF THE INVENTION

The present invention relates to peptides derived from the mitochondrial protein, voltage-dependent anion channel 1 (VDAC), particularly to short bioactive peptides and peptide conjugates comprising a permeability enhancing moiety useful in inducing cell death, particularly in cancerous cell.

BACKGROUND OF THE INVENTION

Voltage-dependent anion channel 1 (VDAC1; mitochondrial porin) is a pore-forming protein found in the outer mitochondrial membrane in all eukaryotic cells. VDAC1 controls cross-talk between mitochondria and the rest of the cell by serving as a gatekeeper for the entry and exit of metabolites. In addition to regulating metabolic and energetic functions of the cell, VDAC1 also provides a point of convergence for a variety of cell survival and death signals, mediated via its association with various ligands and proteins. Moreover, VDAC1 is a key player in mitochondria-mediated apoptosis, participating in the release of mitochondria pro-apoptotic proteins (e.g. cytochrome c, AIF and Smac/DIABLO) to the cytosol and interacting with apoptosis regulatory proteins such as Bcl-2, Bcl-X and hexokinase (HK).

Three mammalian isoforms of VDAC are known, VDAC1, VDAC2 and VDAC3, where VDAC1 is the major isoform expressed in mammalian cells. Blachly-Dysion et al. (Blachly-Dyson E et al., 1993. J Biol Chem. 268(3): 1835-41) disclosed the cloning and functional expression in yeast of two human VDAC isoforms, VDAC1 and VDAC2. U.S. Pat. No. 5,780,235 discloses two VDAC sequences, which were named HACH (Human voltage-dependent Anion Channel), subsequently identified as VDAC2 and VDAC3. That patent provides genetically engineered expression vectors, host cells containing the vector, a method for producing HACH and a method for identifying pharmaceutical compositions inhibiting the expression and activity of HACH and for the use of such compositions for the treatment of cancer and proliferative diseases.

Computer modeling of the VDAC's primary amino acid sequences led to the development of models showing the transmembrane organization of VDAC1, consisting of a single amphipathic N-terminal α-helix and 13 or 16 transmembrane β-strands. These β-strands are connected by several peptide loops of different sizes on both sides of the membrane that serve as potential protein interacting sites. Recently, the three-dimensional structure of isoform 1 of VDAC was determined at atomic resolution by three independent technical approaches, leading to a structure featuring a 19-stranded β-barrel and an N-terminal α-helical region located inside the pore.

Several functional implications of this architecture were suggested. It was proposed that the N-terminal region lies inside the pore yet could move in the open space. The mobility of the N-terminal region was further supported by studies showing that the N-terminal α-helix exhibits motion during voltage-gating, and that anti-VDAC1 antibodies raised against the N-terminal region of the protein interact with membranal VDAC1. It has been also shown that the N-terminal α-helix interacts with apoptosis-regulating proteins of the Bcl-2 family (i.e., Bax, Bcl2 and Bcl-xL) and hexokinase (see, for example, Abu-Hamad S et al. 2009. J Cell Sci 122:1906-1916; Shi Y et al. 2003. Biochem Biophys Res Commun 305:989-996; Arbel N et al. 2012. J Biol Chem. 287(27):23152-61, Arbel N and Shoshan-Barmatz V. 2010. J Biol Chem 285:6053-6062; Geula S et al. 2012. Biochem J. 15:444(3):475-485) and that movement of this VDAC1 segment out of the pore modulated the anti-apoptotic activities of these binding partners. Moreover, cells expressing N-terminal domain-truncated VDAC1 are resistant to apoptosis (Abu-Hamad S et al. 2009, ibid). These findings indicate that the N-terminal domain is required for apoptosis induction, interactions with HK-I, HK-II, Bcl-xL and Bcl-2 and for protection against apoptosis.

The GXXXG motif has been associated with dimerization of proteins including glycophorin A, human carbonic anhydrase, yeast ATP synthase and more. In VDAC1, the GXXXG motif is present in the N-terminus of the channel that forms the α-helix structure.

It was reported that in VDAC1, a glycine-rich sequence (GXXXG), highly conserved in mammals, connects the N-terminal domain to the β-barrel, thus providing the flexibility needed for N-terminal translocation in and out of the pore. GXXXG motif of the VDAC1 N-terminal domain is involved in N-terminal domain translocation out of the VDAC pore and in the oligomerization of VDAC1 (Geula S. et al., 2012, ibid) U.S. Pat. No. 8,440,788 to the inventor of the present invention and co-workers discloses that VDAC1 derived peptides having a point mutation within the GXXXG motif are capable of inhibiting apoptosis.

Apoptosis, also known as programmed cell death, plays a central role in, inter alia, development, immune cell regulation and tissue homeostasis in multicellular organisms. Genetic and molecular analysis from various species has indicated that the apoptotic pathway is highly conserved. In addition to being essential for normal development and maintenance, apoptosis is important in the defense against viral infection and in preventing cancer. Mitochondria play an important role in the regulation of apoptotic cell death. The release of apoptogenic intermediates such as cytochrome c from the intermembranal space into the cytoplasm of a cell initiates a cascade of caspase activation that executes the cell death program. Substantial evidence links VDAC1 to apoptosis and suggests that VDAC1 is a critical player in the release of apoptogenic proteins from mitochondria in mammalian cells (Shoshan-Barmatz V and Gincel D. 2003. Cell Biochem Biophys 39: 279-292; Shoshan-Barmatz V et al. 2010. Molecular Aspects of Medicine 31(3): 227-286; Shoshan-Barmatz V and Ben-Hail D. 2012. Mitochondrion 12(1):24-34; Shoshan-Barmatz V and Golan M. 2012. Current Medicinal Chemistry 19(5):714-35).

Diverse intrinsic cell death signals emanating from various subcellular organelles can induce the release of cytochrome c from mitochondria. The Bcl-2 family of pro- and anti-apoptotic proteins constitutes a decisive control point for apoptosis. Proteins in the Bcl-2 family are major regulators of apoptosis (reviewed in Kim R. 2005. Biochem Biophys Res Commun 333(2):336-43). Members of this family include both pro- and anti-apoptotic proteins and share homology in up to four conserved regions termed Bcl-2 homology (BH) 1-4 domains. The family can be divided into three main sub-classes: anti-apoptotic proteins, pro-apoptotic proteins and BH3-only proteins. The anti-apoptotic proteins, including hexokinase-I (HK-I), Bcl-2 and Bcl-xL, share homology throughout all four BH domains. The pro-apoptotic proteins can be further subdivided and include multi-domain proteins, such as Bax and Bak, which possess sequence homology in BH1-3 domains.

The more distantly related BH3-only proteins appear to be only pro-apoptotic and share sequence homology within the BH3 region, which is required for their apoptotic function. The BH3-only proteins include, for example, BID, NOXA, PUMA and BAD.

It is currently held that anti-apoptotic members of the Bcl-2 family of proteins, such as HK-I, HK-II, Bcl-2 and Bcl-xL, act to promote cell survival by interacting with VDAC. Conversely, pro-apoptotic members of the Bcl-2 family of proteins, including Bak and Bax, may interact with VDAC to promote release of cytochrome c. Because of the pivotal role that mitochondria play in apoptotic cell death, mitochondrial proteins serve as potential targets for apoptosis regulating therapies.

One major obstacle in cancer chemotherapy is inherent, or acquired, resistance, apparently due to the suppression of apoptosis in the cancerous cells. Hexokinase-I (HK-I) is an anti-apoptotic mitochondrial protein that binds to VDAC. Many tumor cells exhibit a high glycolytic rate, which is correlated with a high level of HK-I expression. It is believed that the overexpression of anti-apoptotic proteins such as HK-I in cancer cells is a self-defense mechanism of those cells and is related to the cell's resistance to chemotherapy. In B-chronic lymphocytic leukemia (CLL), the failure of mature B cells to undergo apoptosis constitute the primary cellular defect leading to the cancer disease (Montserrat E and Moreno C. 2008. Ann Oncol 2008 Sep. 19, Suppl 7:vii320-325).

The anti-apoptotic proteins of the Bcl-2 family, such as Bcl-2, Bcl-xL and Mcl-1 and XIAP are overexpressed in CLL, whereas the pro-apoptotic protein Bax in underexpressed (Kitada S et al. 1998. Blood 91:3379-3389).

Certain compositions related to VDAC1 and use thereof for either inhibiting or inducing apoptosis are known in the art. U.S. Patent Application Publication No. 2005/0085420 discloses methods of inhibiting apoptosis by promoting formation of a BAK/VDAC2 complex, and methods of promoting apoptosis by disrupting formation of a BAK/VDAC2 complex. The VDAC2/BAK inhibitor compound is, for example, a BH3 domain peptide, a BH3 domain-only mutein, an anti-VDAC2 antibody, a VDAC2 mutein and the like.

U.S. Patent Application Publication No. 2005/0234116 discloses small molecule compounds with utility as VDAC regulators, in particular as apoptosis suppressors.

U.S. Pat. Nos. 8,119,601 and 8,648,045 to the inventor of the present invention and others disclose VDAC variants and VDAC derived peptides as well as polynucleotides encoding same useful in inducing or regulating apoptosis and to pharmaceutical compositions comprising same useful in the treatment of diseases associated with aberrant apoptosis.

A publication of the inventor of the present invention and co-workers, published after the priority date of the present invention, demonstrates that VDAC1-based peptides, including short peptides selectively induced cells death of peripheral mononuclear cells (PBMC) from CLL patients while exhibiting minor effects on PBMCs from healthy donor (Prezma T et al. 2013 Sep. 19; 4:e809. doi: 10.1038/cddis.2013.316).

There remains an unmet need for improved therapeutic agents that specifically induce cancer cell apoptosis, particularly for improved peptides with improved pharmacokinetic characteristics for inducing cancer cell death.

SUMMARY OF THE INVENTION

The present invention provides, for the first time, short synthetic peptides and peptide conjugates that are based on VDAC1 N-terminal domain, effective in inducing cell death. The improved peptides provided are shorter and/or more stable and/or more active compared to previously disclosed peptides, making them better candidates as therapeutic agents for the treatment of diseases characterized by cell hyperproliferation or resistance to cell death, particularly cancer.

The present invention is based in part on the unexpected discovery that synthetic short peptides based on VDAC1 N-terminal domain maintain the ability to induce cell death, particularly of cancerous cells. Furthermore, synthetic peptides composed of amino acids having the D configuration showed increased activity compared to the hitherto known peptide derived from amino acids residues 1-26 of human VDAC1 N-terminal domain (SEQ ID NO:1).

According to a first aspect, the present invention provides a peptide of 5-25 amino acids comprising a contiguous sequence derived from amino acids residues 1-26 of human VDAC1 N-terminal domain comprising the GXXXG motif, wherein G is a glycine residue.

It is to be understood that the present invention encompasses peptides having any length between 5-25 amino acids (i.e. 6, 7, 8, 9, 10, 1 and up to 25 amino acids). According to certain exemplary embodiments, the peptide comprises 8 amino acids. According to other exemplary embodiments, the peptide comprises 12 amino acids. According to additional exemplary embodiments, the peptide comprises 16 amino acids. According to further embodiments, the peptide comprises 22 amino acids.

According to certain embodiments, the peptide is capable of inducing cell death. According to some embodiments, the peptide induces apoptosis or enhances sensitivity to an apoptosis-inducing reagent. Non-limiting examples of apoptosis-inducing reagents include staurosporine (STS), curcumin, doxorubicin and paclitaxel.

According to other embodiments, the peptide impairs the cell energy production. According to yet additional embodiments, cell death is a result of a combination of apoptosis induction and impairment of the cell energy production.

According to some embodiments, the GXXXG motif (SEQ ID NO:2) comprises the amino acid sequence GYGFG (SEQ ID NO:3), wherein G is a glycine residue or a functional modified glycine residue, Y is a tyrosine residue or a functional modified tyrosine residue and F is a phenylalanine residue or a functional modified phenylalanine residue.

According to certain exemplary embodiments, the peptide comprises the amino acid sequence set forth in SEQ ID NO:4. According to other exemplary embodiments, the peptide comprises the amino acid sequence set forth in SEQ ID NO:5. According to additional exemplary embodiments, the peptide comprises the amino acid sequence set forth in SEQ ID NO:6. According to yet additional exemplary embodiments, the peptide comprises the amino acid sequence set forth in SEQ ID NO:7.

According to yet additional embodiments, the peptide consists of the amino acid sequence set forth in any one of SEQ ID NO:4, SEQ ID NO:5, SEQ ID NO:6 and SEQ ID NO:7. Each possibility represents a separate embodiment of the present invention.

In one embodiment the peptides of the invention comprise an amino acid sequence that modulates the interaction between VDAC1 and anti-apoptotic proteins. Certain anti-apoptotic proteins are known in the art and include hexokinase-I (HK-I), HK-II, Bcl-2, Bcl-2A1, Bcl-2L1, Bcl2-L10, Bcl-2L11, Bcl-2L2, Bcl-xL and Bcl-W.

It is yet another object of the present invention to provide short peptides based on the sequence of VDAC1 N-terminal domain and conjugates thereof comprising peptidomimetic compounds having further improved stability and cell permeability properties. Non limiting examples of such compounds include N-alkylation of selected peptide residues, side-chain modifications of selected peptide residues, non-natural amino acids, use of carbamate, urea, sulfonamide and hydrazine for peptide bond replacement, and incorporation of non-peptide moieties including but not limited to piperidine, piperazine and pyrrolidine, through a peptide or non-peptide bond. Modified bonds between amino acid residues in peptidomimetics according to the present invention may be selected from the group consisting of amide, urea, carbamate and hydrazine or sulfonamide bond. Unless explicitly stated otherwise the bonds between the amino acid residues are all amide bonds.

Stability to enzymatic degradation is an important factor in designing synthetic peptides to be used as therapeutic agents. The D-stereoisomers of amino acids are known to be more stable to such degradation. Unexpectedly, the present invention now shows that the peptides of the invention, synthesized from D-modified amino acids, are active, and sometimes more active in inducing cell death compared to a corresponding peptide comprising the native L-amino acids.

Thus, according to certain embodiments, the peptides of the invention are all L-stereomeric peptides, comprising only L-amino acids. According to other embodiments, the peptides are D-L stereomeric peptides, comprising a combination of D- and L-amino acids. According to yet additional embodiments, the peptides are all D-stereomeric peptides, comprising only D-amino acids.

According to certain embodiments, the peptide based on the VDAC1 N-terminal domain is conjugated to a cell permeability moiety covalently connected to the peptide via a direct bond or via a linker, to form a peptide conjugate.

According to certain currently exemplified embodiments, the cell permeability moiety according to the present invention is connected to the C-terminus free group of the active peptide. The moiety may be linked directly to the peptide or through a linker or a spacer. Without wishing to be bound by any specific theory or mechanism of action, a free N-terminus group is required, as adding the peptidic cell permeability moiety at the C-terminus yielded less active peptide.

Any moiety known in the art to facilitate permeability actively or passively or enhance permeability of the compound into cells may be used for conjugation with the peptide core according to the present invention. Non-limiting examples include hydrophobic moieties such as fatty acids, steroids and bulky aromatic or aliphatic compounds; moieties which may have cell-membrane receptors or carriers, such as steroids, vitamins and sugars, natural and non-natural amino acids, liposomes, nanoparticles and transporter peptides. According to certain exemplary embodiments, the cell permeability enhancing moiety is a cell penetrating peptide (CPP). In one exemplary embodiment the CPP is an amino acid sequence comprising the *Drosophila* antennapedia (Antp) domain or a fragment thereof. In certain exemplary embodiments the Antp domain comprises the amino acid sequence as set forth in SEQ ID NO:8. According to these embodiments, the peptide conjugate comprises an amino acid sequence selected from the group consisting of SEQ ID NO:9, SEQ ID NO:10, SEQ ID NO:11 and SEQ ID NO:12.

According to additional exemplary embodiments, the CPP comprises a fragment of the TfR domain recognized by the human transferrin receptor (Tf) having the amino acid sequence HAIYPRH set forth in SEQ ID:13. According to theses embodiments, the peptide conjugate comprises an amino acid sequence selected from the group consisting of SEQ ID NO:14, SEQ ID NO:15, SEQ ID NO:16 and SEQ ID NO:17. Each possibility represents a separate embodiment of the present invention.

According to certain exemplary embodiment, a peptide conjugate capable of inducing cell death is disclosed, the conjugate consisting of a cell-penetrating peptide covalently connected, through an optional linker, to the C-terminus of a peptide of 5-25 amino acids comprising a contiguous sequence derived from amino acids 1-26 of human VDAC1 N-terminal domain, comprising the GXXXG motif, wherein G is a glycine residue.

According to certain exemplary embodiments, the conjugate consists of the amino acid sequence set forth in SEQ ID NO:9. According to other certain exemplary embodiments, the conjugate consists of the amino acid sequence set forth in SEQ ID NO:10. According to yet additional exemplary embodiments, the conjugate consists of the amino acid sequence set forth in SEQ ID NO:11. According to further exemplary embodiments, the conjugate consists of the amino acid sequence set forth in SEQ ID NO:12. According to some exemplary embodiments, the conjugate consists of the amino acid sequence set forth in SEQ ID NO:14. According to other exemplary embodiments, the conjugate consists of the amino acid sequence set forth in SEQ ID NO:15. According to yet additional exemplary embodiments, the conjugate consists of the amino acid sequence set forth in SEQ ID NO:16. According to further exemplary embodiments, the conjugate consists of the amino acid sequence set forth in SEQ ID NO:17.

It is to be explicitly understood that previously known peptides are excluded from the present invention.

Cyclic versions of the peptides disclosed herein are also within the scope of the present invention.

According to another aspect the present invention provides a pharmaceutical composition comprising at least one peptide of 5-25 amino acids comprising a contiguous sequence derived from amino acids 1-26 of human VDAC1 N-terminal domain, comprising the GXXXG motif, wherein G is a glycine residue, further comprising a therapeutically acceptable diluent or a carrier.

According to certain embodiment, the pharmaceutical composition comprises a peptide having the amino acid sequence set forth in any one of SEQ ID NO:4, SEQ ID NO:5, SEQ ID NO:6 and SEQ ID NO:7. Each possibility represents a separate embodiment of the present invention.

According to certain exemplary embodiments, the present invention provides a pharmaceutical composition comprising at least one peptide conjugate comprising a peptide of 5-25 amino acid comprising a contiguous sequence derived from amino acids 1-26 of human VDAC1 N-terminal domain, comprising the GXXXG motif, wherein G is a glycine residue, and cell permeability moiety, further comprising a therapeutically acceptable diluents or carrier. According to certain embodiments, the cell permeability moiety is CPP. According to further exemplary embodiments, the CPP comprises the Antp domain having the amino acid sequence set forth in SEQ ID NO:8 or a fragment thereof. According to yet additional embodiments, the CPP comprises the Tf sequence having the amino acid sequence set forth in SEQ ID NO:13.

According to some exemplary embodiments, the pharmaceutical composition comprises at least one peptide conjugate having an amino acid sequence selected from the group consisting of SEQ ID NO:9, SEQ ID NO:10, SEQ ID NO:11, SEQ ID NO:12, SEQ ID NO:14, SEQ ID NO:15, SEQ ID NO:16 and SEQ ID NO:17 further comprising a therapeutically acceptable diluents or carrier. Each possibility represents a separate embodiment of the present invention. According to other exemplary embodiments, the pharmaceutical composition comprises at least one peptide conjugate consisting of the amino acid sequence selected from the group consisting of SEQ ID NO:9, SEQ ID NO:10, SEQ ID NO:11 and SEQ ID NO:12, further comprising a therapeutically acceptable diluents or carrier. Each possibility represents a separate embodiment of the present invention.

In certain embodiments the pharmaceutical composition comprises a VDAC1-based peptide according to the present invention and a shielding particle. In certain embodiments the shielding particle comprises polyethyleneglycol (PEG) and/or lipids.

In certain embodiments the pharmaceutical composition comprises an encapsulated VDAC1-based peptide according to the present invention. In certain embodiments the VDAC1-based peptide is encapsulated into a vesicle, or into immunoliposomes.

The pharmaceutical compositions of the present invention are useful for treating diseases associated with aberrant apoptosis and/or cell hyperproliferation, particularly cancer.

In yet another aspect the present invention provides a method for treating a subject suffering from a disease associated with aberrant apoptosis and/or cell hyperproliferation, the method comprising administering to a subject in need thereof a pharmaceutical composition comprising a therapeutically effective amount of at least one peptide of 5-25 amino acids comprising a contiguous sequence derived from amino acids 1-26 of human VDAC1 N-terminal domain, comprising the GXXXG motif, wherein G is a glycine residue or a conjugate thereof.

In some embodiments the disease is a cancerous disease including chemo- and radiotherapy-resistant cancer. According to certain typical embodiments, the disease associated with aberrant apoptosis is cancer. According to further typical embodiments, the cancer is selected from the group consisting of leukemia, hepatocellular carcinoma, pancreatic cancer, glioblastoma, cervical carcinoma, malignant melanoma, alveolar basal cell adenocarcinoma, bronchial veolar carcinoma, prostate cancer and breast cancer. Each possibility represents a separate embodiment of the present invention.

According to certain embodiments, the present invention provides a method for treating a subject having chronic lymphocytic leukemia, the method comprising administering to the subject a pharmaceutical composition comprising a therapeutically effective amount of at least one peptide of 5-25 amino acids comprising a contiguous sequence derived from amino acids 1-26 of human VDAC1 N-terminal domain, comprising the GXXXG motif, wherein G is a glycine residue or a conjugate thereof. According to certain embodiments, the peptide comprises the amino acid sequence set forth in any one of SEQ ID NOs:4-7. According to further embodiments, the pharmaceutical composition comprises a peptide conjugate having the amino acid sequence set forth in any one of SEQ ID NOs:9, 10, 11, 12, 14, 15, 16 and 17. Each possibility represents a separate embodiment of the present invention.

According to other embodiments, the present invention provides a method for treating a subject having glioblastoma, the method comprising administering to the subject a pharmaceutical composition comprising a therapeutically effective amount of at least one peptide of 5-25 amino acids comprising a contiguous sequence derived from amino acids 1-26 of human VDAC1 N-terminal domain, comprising the GXXXG motif, wherein G is glycine residue or a conjugate thereof. According to certain embodiments, the peptide comprises the amino acid sequence set forth in any one of SEQ ID NOs: 4-7. According to further embodiments, the pharmaceutical composition comprises a peptide conjugate having the amino acid sequence set forth in any one of SEQ ID NOs: 9, 10, 11, 12, 14, 15, 16 and 17. Each possibility represents a separate embodiment of the present invention.

According to yet other embodiments, the present invention provides a method for treating a subject having prostate cancer, the method comprising administering to the subject a pharmaceutical composition comprising a therapeutically effective amount of at least one peptide of 5-25 amino acids comprising a contiguous sequence derived from amino acids 1-26 of human VDAC1 N-terminal domain, comprising the GXXXG motif, wherein G is a glycine residue or a modified glycine residue or a conjugate thereof. According to certain embodiments, the peptide comprises the amino acid sequence set forth in any one of SEQ ID NOs: 4-7. According to further embodiments, the pharmaceutical composition comprises a peptide conjugate having the amino acid sequence set forth in any one of SEQ ID NOs: 9, 10, 11, 12, 14, 15, 16 and 17. Each possibility represents a separate embodiment of the present invention.

According to additional aspect, the present invention provides the use of at least one peptide of 5-25 amino acids comprising a contiguous sequence derived from t amino acids 1-26 of human VDAC1 N-terminal domain, comprising the GXXXG motif, wherein G is a glycine residue or a conjugate thereof for the preparation of a medicament useful in treating a disease associated with aberrant apoptosis and/or cell hyperproliferation. According to certain embodiments, the disease is cancer. According to certain exemplary embodiments, the medicament is useful for treating a cancerous disease selected from the group consisting of chronic lymphocytic leukemia, prostate cancer and glyoblastoma. Each possibility represents a separate embodiment of the present invention.

According to yet additional aspect, the present invention provide a method of inducing cancer cell death comprising applying to the cancer cells at least one peptide of 5-25 amino acids comprising a contiguous sequence derived from amino acids 1-26 of human VDAC1 N-terminal domain, comprising the GXXXG motif, wherein G is a glycine residue or a conjugate thereof. According to certain embodiments, the peptide comprises the amino acid sequence set forth in any one of SEQ ID NO:4, SEQ ID NO:5, SEQ ID NO:6 and SEQ ID NO:7. According to other embodiments, the peptide conjugate comprises the amino acids sequence set forth in any one of SEQ ID NO:9, SEQ ID NO:10, SEQ ID NO:11, SEQ ID NO:12, SEQ ID NO:14, SEQ ID NO:15, SEQ ID NO:16 and SEQ ID NO:17. Each possibility represents a separate embodiment of the present invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 3A: human glioblastoma U-87 cells. FIG. 3B: human neuroblastoma SH-SY5Y cells. FIG. 3C: rat glioblastoma C6 cells. Peptide D-Δ1-14N-Ter-Antp: amino acids 15-26 of the VDAC1 N-terminal domain with Antp (SEQ ID NO:9). Data represent mean values, n=2. The previously disclosed LP4 peptide conjugated to Tf (Tf-D-LP4 peptide, SEQ ID NO:20) was used as a reference of activity.

FIG. 6A: cells analyzed for Δψ following incubation for 30 min with or without the potentiometric fluorescent dye tetramethylrhodamine methyl ester (TMRM). Fluorescence intensity of mitochondrial Δψ is presented as percentage of control. FIG. 6B: cells were analyzed for cellular ATP level using a specific kit and plate reader. ATP amount is and is presented as percentage of control.

FIG. 8A: Control FIG. 8B: cell incubated with 2.8 μM peptide D-Δ(1-14) N-Ter-Antp.

FIG. 10A shows the tumor volume in mm3. FIG. 10B shows the reduction in tumor size of treated tumors as percentage of control.

DETAILED DESCRIPTION OF THE INVENTION

Figure 1:
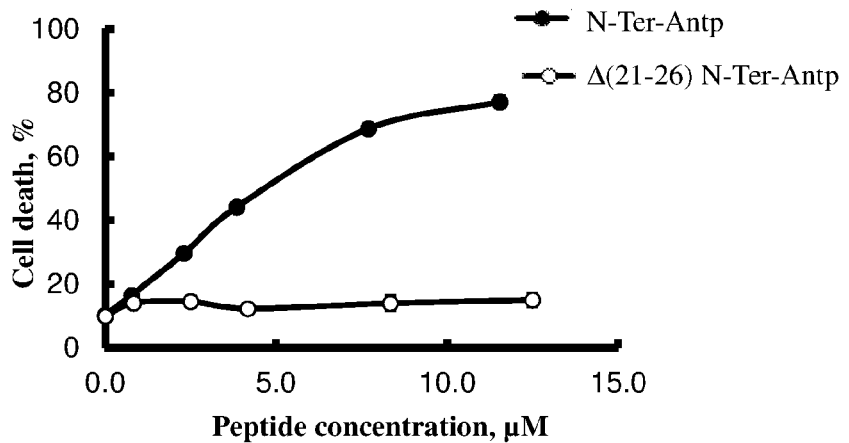
FIG. 1 demonstrates that the amino acid sequence motif GXXXG in necessary for cell death induction by the VDAC1-derived peptides. MEC-1 cells were incubated with different peptide concentrations for 90 min in a serum-free medium. Peptide N-Ter-Antp: complete VDAC1 N-terminal domain (1-26 amino acids) with Antp (SEQ ID NO:21). Peptide Δ(21-26) N-Ter-Antp: amino acids 1-20 of the VDAC1 N-terminal domain with Antp (SEQ ID NO:22). Data represent mean values±S.E. (n=3).

As a result of major advances in organic chemistry and in molecular biology, many bioactive peptides can now be prepared in quantities sufficient for pharmacological and clinical use. Thus in the last few years new methods have been established for the treatment and diagnosis of illnesses in which peptides have been implicated. However, the use of peptides as therapeutic and diagnostic agents is limited by the following factors: a) tissue penetration; b) low metabolic stability towards proteolysis in the gastrointestinal tract and in serum; c) poor absorption after oral ingestion, in particular due to their relatively high molecular mass or the lack of specific transport systems or both; d) rapid excretion through the liver and kidneys; and e) undesired side effects in non-target organ systems, since peptide receptors can be widely distributed in an organism.

The present invention now discloses short synthetic peptides effective in inducing apoptosis and cell death. The inventors of the present invention and co-workers previously disclosed an apoptosis-inducing peptide derived from human VDAC1 comprising amino acids 1-26 of the protein N-terminus Unexpectedly, the present invention now shows that peptides as short as eight (8) amino acids retains and/or improve the capability to induce apoptosis and cell death, with the proviso that the peptide comprises the amino acid motif GXXXG. The present invention further disclose peptide conjugates comprising the VDAC-based peptides and a cell penetration enhancing moiety, particularly cell penetrating peptides. The short peptides of the invention, being easy to synthesize and stable are highly suitable for use as therapeutic means of disease characterized by cell hyperproliferation, particularly cancer. Indeed the present invention now demonstrated that the peptides of the invention are active in vivo, reducing the growth of glioblastoma xenografts.

DEFINITIONS

For convenience certain terms employed in the specification, examples and claims are described herein.

The terms "VDAC1" and "hVDAC1" are used herein interchangeably and refer to the human voltage-depended anion channel isoform 1 (hVDAC1) of a highly conserved family of mitochondrial porin. Four VDAC isoforms, encoded by three genes, are known to date; as used herein, the terms "VDAC1" and "hVDAC1" refer to a 283 amino acid protein (NP_003365) having the amino acids sequence set forth in SEQ ID NO:18. The term "VDAC1 N-terminal domain" refers to the protein N-terminal amino acids M1-L6 set forth in SEQ ID NO:1.

The term "peptide" as used herein is meant to encompass natural, non-natural and/or chemically modified amino acid residues, each residue being characterized by having an amino and a carboxy terminus, connected one to the other by peptide or non-peptide bonds. The amino acid residues are represented throughout the specification and claims by either one or three-letter codes, as is commonly known in the art. The peptides of the present invention are preferably utilized in a linear form, although it will be appreciated that in cases where cyclization does not severely interfere with peptide characteristics, cyclic forms of the peptide can also be utilized.

The amino acids used in this invention are those which are available commercially or are available by routine synthetic methods. Certain residues may require special methods for incorporation into the peptide, and sequential, divergent and convergent synthetic approaches to the peptide sequence are useful in this invention. Natural coded amino acids and their derivatives are represented by three-letter codes according to IUPAC conventions. When there is no indication, either the L or D isomers may be used. Peptides comprising D-amino acids are designated as "D-peptides".

Conservative substitutions of amino acids as known to those skilled in the art are within the scope of the present invention. Conservative amino acid substitutions includes replacement of one amino acid with another having the same type of functional group or side chain e.g. aliphatic, aromatic, positively charged, negatively charged. These substitutions may enhance oral bioavailability, affinity to the target protein, metabolic stability, penetration into the central nervous system, targeting to specific cell populations and the like. One of skill will recognize that individual substitutions, deletions or additions to peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another: Alanine (A), Serine (S), Threonine (T); Aspartic acid (D), Glutamic acid (E); Asparagine (N), Glutamine (Q); Arginine (R), Lysine (K); Isoleucine (I), Leucine (L), methionine (M), Valine (V); and Phenylalanine (F), Tyrosine (Y), Tryptophan (W).

Also included within the scope of the invention are salts of the peptides and/or peptide conjugates, analogs, and chemical derivatives of the peptides and peptide conjugates of the invention.

As used herein the term "salts" refers to both salts of carboxyl groups and to acid addition salts of amino or guanido groups of the peptide molecule. Salts of carboxyl groups may be formed by means known in the art and include inorganic salts, for example sodium, calcium, ammonium, ferric or zinc salts, and the like, and salts with organic bases such as salts formed for example with amines such as triethanolamine, piperidine, procaine, and the like. Acid addition salts include, for example, salts with mineral acids such as, for example, acetic acid or oxalic acid. Salts describe here also ionic components added to the peptide solution to enhance hydrogel formation and/or mineralization of calcium minerals.

A "chemical derivative" as used herein refers to peptides or peptide conjugates containing one or more chemical moieties not normally a part of the peptide molecule such as esters and amides of free carboxy groups, acyl and alkyl derivatives of free amino groups, phospho esters and ethers of free hydroxy groups. Such modifications may be introduced into the molecule by reacting targeted amino acid residues of the peptide with an organic derivatizing agent that is capable of reacting with selected side chains or terminal residues. Exemplary chemical derivatives include peptides that have been phosphorylated, C-termini amidated or N-termini acetylated.

"Functional derivatives" of the peptides or peptide conjugates of the invention as used herein covers derivatives which may be prepared from the functional groups which occur as side chains on the residues or the N- or C-terminal groups, by means known in the art, and are included in the invention as long as they remain pharmaceutically acceptable, i.e., they do not destroy the activity of the peptide or peptide conjugate, do not confer toxic properties on compositions containing it and do not adversely affect the antigenic properties thereof. These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups) or O-acyl derivatives of free hydroxyl group (for example that of seryl or threonyl residues) formed by reaction with acyl moieties.

The term "peptide analog" indicates molecule which has the amino acid sequence according to the invention except for one or more amino acid changes or one or more modification/replacement of an amide bond. Peptide analogs include amino acid substitutions and/or additions with natural or non-natural amino acid residues, and chemical modifications which do not occur in nature. Peptide analogs include peptide mimetics. A peptide mimetic or "peptidomimetic" means that a peptide according to the invention is modified in such a way that it includes at least one non-coded residue or non-peptidic bond. Such modifications include, e.g., alkylation and more specific methylation of one or more residues, insertion of or replacement of natural amino acid by non-natural amino acids, replacement of an amide bond with other covalent bond. A peptidomimetic according to the present invention may optionally comprises at least one bond which is an amide-replacement bond such as urea bond, carbamate bond, sulfonamide bond, hydrazine bond, or any other covalent bond. The design of appropriate "analogs" may be computer assisted. Additional peptide analogs according to the present invention comprise a specific peptide or peptide analog sequence in a reversed order, namely, the amino acids are coupled in the peptide sequence in a reverse order to the amino acids order which appears in the native protein or in a specific peptide or analog identified as active. Whether completely or partially non-peptide, peptidomimetics according to this invention provide a spatial arrangement of chemical moieties that closely resembles the three-dimensional arrangement of groups in the peptide on which the peptidomimetic is based. As a result of this similar active-site structure, the peptidomimetic has effects on biological systems, which are similar to the biological activity of the peptide.

A modified amino acid residue is an amino acid residue in which any group or bond was modified by deletion, addition, or replacement with a different group or bond, as long as the functionality of the amino acid residue is preserved or if functionality changed (for example replacement of tyrosine with substituted phenylalanine) as long as the modification did not impair the activity of the peptide containing the modified residue.

"A peptide conjugate" according to the present invention, denotes a molecule comprising a sequence of a peptide of 5-25 amino acids comprising a contiguous sequence derived from the N-terminal domain of VDAC1, comprising the GXXXG motif to which another moiety, either peptidic or non peptidic, is covalently bound, directly or via a linker According to certain currently preferred embodiments, the moiety is a peptidic cell-permeability moiety.

The term "linker" denotes a chemical moiety whose purpose is to link, covalently, a cell permeability enhancing moiety and a peptide or peptidomimetic. Linker denotes a direct chemical bond or a spacer. The spacer may be used to allow distance between the permeability moiety and the peptide, or it is a chemical bond of any type.

"Permeability" refers to the ability of an agent or substance to penetrate, pervade, or diffuse through a barrier, membrane, or a skin layer. A "cell permeability moiety" or a "cell-penetration moiety" or "cell permeability enhancing moiety" refers to any molecule known in the art which is able to facilitate or enhance penetration of molecules through membranes. Non-limitative examples include: hydrophobic moieties such as lipids, fatty acids, steroids and bulky aromatic or aliphatic compounds; moieties which may have cell-membrane receptors or carriers, such as steroids, vitamins and sugars, natural and non-natural amino acids, transporter peptides, nanoparticles and liposomes.

According to certain exemplary embodiments, the cell permeability moiety is peptidic. A novel carrier system that originates from membrane shuttling proteins has several advantages for targeted delivery. This "transport system" is mediated by the so-called CPPs, (Cell Penetrating Peptides or Cell Penetration Peptides), which consist of short peptide sequences that rapidly translocate molecules, including large molecules into the cell interior in a seemingly energy- and receptor-independent manner CPPs have low toxicity and a high yield of delivery. Exemplary CPPs are the Antp domain described herein above having SEQ ID NO:8, the HIV-1 transcriptional factor TAT, VP22 from HSV-1 and a fragment of the transferrin (Tf) domain (having the amino acid sequence set forth in SEQ ID NO:13) recognized by transferrin receptor which is highly expressed in several cancerous cell types.

It is to be explicitly understood that other types of cell permeability moieties can be used according to the teachings of the present invention.

According to some embodiment, the cell penetration moiety is a hydrophobic moiety that may preferably comprise a lipid moiety or an amino acid moiety. According to a specific embodiment the hydrophobic moiety is selected from the group consisting of: phospholipids, steroids, sphingosines, ceramides, octyl-glycine, 2-cyclohexylalanine, benzolylphenylalanine, propionoyl ($C_3$); butanoyl ($C_4$); pentanoyl ($C_5$); caproyl ($C_6$); heptanoyl ($C_7$); capryloyl ($C_8$); nonanoyl ($C_9$); capryl ($C_{10}$); undecanoyl ($C_{11}$); lauroyl ($C_{12}$); tridecanoyl ($C_{13}$); myristoyl ($C_{14}$); pentadecanoyl ($C_{15}$); palmitoyl ($C_{16}$); phtanoyl (($CH_3$)$_4$); heptadecanoyl ($C_{17}$); stearoyl ($C_{18}$); nonadecanoyl ($C_{19}$); arachidoyl ($C_{20}$); heniecosanoyl ($C_{21}$); behenoyl ($C_{22}$); trucisanoyl ($C_{23}$); and lignoceroyl ($C_{24}$); wherein said hydrophobic moiety is attached to said chimeric polypeptide with amide bonds, sulfhydryls, amines, alcohols, phenolic groups, or carbon-carbon bonds.

Other examples for lipidic moieties which may be used according to the present invention: Lipofectamine, Transfectace, Transfectam, Cytofectin, DMRIE, DLRIE, GAP-DLRIE, DOTAP, DOPE, DMEAP, DODMP, DOPC, DDAB, DOSPA, EDLPC, EDMPC, DPH, TMADPH, CTAB, lysyl-PE, DC-Cho, -alanyl cholesterol; DCGS, DPPES, DCPE, DMAP, DMPE, DOGS, DOHME, DPEPC, Pluronic, Tween, BRIJ, plasmalogen, phosphatidylethanolamine, phosphatidylcholine, glycerol-3-ethylphosphatidylcholine, dimethyl ammonium propane, trimethyl ammonium propane, diethylammonium propane, triethylammonium propane, dimethyldioctadecylammonium bromide, a sphingolipid, sphingomyelin, a lysolipid, a glycolipid, a sulfatide, a glycosphingolipid, cholesterol, cholesterol ester, cholesterol salt, oil, N-succinyldioleoylphosphatidylethanolamine, 1,2-dioleoyl-sn-glycerol, 1,3-dipalmitoyl-2-succinylglycerol, 1,2-dipalmitoyl-sn-3-succinylglycerol, 1-hexadecyl-2-palmitoylglycerophosphatidylethanolamine, palmitoylhomocystiene, N,N'-Bis(dodecyaminocarbonylmethylene)-N,N'-bis((-N,N,N-trimethylammoniumethyl-aminocarbonylmethylene)ethylenediamine tetraiodide; N,N"-Bis(hexadecylaminocarbonylmethylene)-N,N',N"-tris((-N,N,N-trimethylammonium-ethylaminocarbonylmethyl-enediethylenetriamine hexaiodide; N,N'-Bis(dodecylaminocarbonylmethylene)-N,N"-bis((-N,N,N-trimethylammonium ethylaminocarbonylmethylene) cyclohexylene-1,4-diamine tetraiodide; 1,7,7-tetra-((-N,N,N,N-tetramethylammoniumethylamino-carbonylmethylene)-3-hexadecylaminocarbonyl-methylene-1,3,7-triaazaheptane heptaiodide; N,N,N',N'-tetra((-N,N,N-trimethylammonium-ethylaminocarbonylmethylene)-N'-(1,2-dioleoylglycero-3-phosphoethanolamino carbonylmethylene) diethylenetriamine tetraiodide; dioleoylphosphatidylethanolamine, a fatty acid, a lysolipid, phosphatidylcholine, phosphatidylethanolamine, phosphatidylserine, phosphatidylglycerol, phosphatidylinositol, a sphingolipid, a glycolipid, a glucolipid, a sulfatide, a glycosphingolipid, phosphatidic acid, palmitic acid, stearic acid, arachidonic acid, oleic acid, a lipid bearing a polymer, a lipid bearing a sulfonated saccharide, cholesterol, tocopherol hemisuccinate, a lipid with an ether-linked fatty acid, a lipid with an ester-linked fatty acid, a polymerized lipid, diacetyl phosphate, stearylamine, cardiolipin, a phospholipid with a fatty acid of 6-8 carbons in length, a phospholipid with asymmetric acyl chains, 6-(5-cholesten-3b-yloxy)-1-thio-b-D-galactopyranoside, digalactosyldiglyceride, 6-(5-cholesten-3b-yloxy)hexyl-6-amino-6-deoxy-1-thio-b-D-galactopyranoside, 6-(5-cholesten-3b-yloxy)hexyl-6-amino-6-deoxyl-1-thio-a-D-mannopyranoside, 12-(((7'-diethylamino-coumarin-3-yl)carbonyl)methylamino)-octadecanoic acid; N-[12-(((7'-diethylaminocoumarin-3-yl)carbonyl)methyl-amino) octadecanoyl]-2-aminopalmitic acid; cholesteryl)4'-trimethyl-ammonio)butanoate; N-succinyldioleoyl-phosphatidylethanolamine; 1,2-dioleoyl-sn-glycerol; 1,2-dipalmitoyl-sn-3-succinyl-glycerol; 1,3-dipalmitoyl-2-succinylglycerol, 1-hexadecyl-2-palmitoylglycero-phosphoethanolamine, and palmitoylhomocysteine.

As used herein the term "apoptosis" or "apoptotic cell death" refers to programmed cell death which can be characterized by cell shrinkage, membrane blebbing and chromatin condensation culminating in cell fragmentation. Cells undergoing apoptosis also display a characteristic pattern of DNA cleavage. Alternatively, apoptosis can be characterized indirectly by changes in the activity or expression of members of the apoptotic pathway, e.g. increased mitochondrial release of cytochrome c. A non-limiting example of apoptosis-inducing reagents known in the art includes actinomycin D, antibiotic A-23187, b-lapachone, Camptothecin, ceramide, curcumin, dexamethasone, etoposide (Etopophos®, Vepesid®), Hypericin, prostaglandin A2, S-Nitrosoglutathione, staurosporin, sulindac sulfide, sulindac sulfone, paclitaxel (Taxol®), vinblastine sulfate, vincristine sulfate, 15(S)-HPETE, 4-hydroxyphenyl retinamide, betulinic acid and the like.

As exemplified herein below, the peptide conjugates of the invention are highly active in inducing cell death. Furthermore, as exemplified with the prostate cell line PC3 (FIG. 5), the peptide conjugate D-Δ1-14N-Ter-Antp was much more effective in inducing cancer cell death ($IC_{50}$=1.51 µM) compared to non-malignant cells TRex-293 ($IC_{50}$>14.31 µM).

According to a first aspect, the present invention provides a peptide of 5-25 amino acids comprising a contiguous sequence derived from the N-terminal domain of VDAC1, comprising the GXXXG motif, wherein G is a glycine residue.

According to some embodiments, the GXXXG motif (SEQ ID NO:2) comprises the amino acid sequence GYGFG (SEQ ID NO:3), wherein G is a glycine or a functional modified glycine residue, Y is tyrosine residue or a functional modified tyrosine residue and F is phenylalanine residue or a functional modified phenylalanine residue.

According to certain exemplary embodiments, the peptide comprises the amino acid sequence set forth in SEQ ID NO:4. According to other exemplary embodiments, the peptide comprises the amino acid sequence set forth in SEQ ID NO:5. According to additional exemplary embodiments, the peptide comprises the amino acid sequence set forth in SEQ ID NO:6. According to yet additional exemplary embodiments, the peptide comprises the amino acid sequence set forth in SEQ ID NO:7.

According to certain embodiments, the peptide based on the VDAC1 N-terminal domain is conjugated to a cell permeability moiety covalently connected to the peptide via a direct bond or via a linker, to form a peptide conjugate.

According to certain exemplary embodiments, the cell permeability enhancing moiety is a cell penetrating peptide (CPP). In one exemplary embodiment the CPP is an amino acid sequence comprising the *Drosophila* antennapedia (Antp) domain or a fragment thereof. In certain exemplary embodiments the Antp domain comprises the amino acid sequence as set forth in SEQ ID NO:8. According to these embodiments, the present invention discloses a peptide conjugate comprising an amino acid sequence selected from the group consisting of SEQ ID NO:9, SEQ ID NO:10, SEQ ID NO:11 and SEQ ID NO:12.

According to additional exemplary embodiments, the CPP comprises a fragment of the TfR domain recognized by the human transferrin receptor (Tf) having the amino acid sequence HAIYPRH set forth in SEQ ID:13. According to theses embodiments, the present invention discloses a peptide conjugate comprising an amino acid sequence selected from the group consisting of SEQ ID NO:14, SEQ ID NO:15, SEQ ID NO:16 and SEQ ID NO:17. Each possibility represents a separate embodiment of the present invention.

Not only that the short peptides of the invention were active, the activity was preserved and even improved when the peptides were synthesized from D-amino acids (Table 3). D-stereomeric peptides are less prone to enzymatic digestion compared to the native-L-stereomeric peptides, making the peptides of the invention suitable for use as therapeutic agents.

According to another aspect the present invention provides a pharmaceutical composition comprising at least one peptide of 5-25 amino acids comprising a contiguous sequence derived from the N-terminal domain of VDAC1, comprising the GXXXG motif, wherein G is a glycine residue, further comprising a therapeutically acceptable diluent or a carrier.

According to certain embodiment, the pharmaceutical composition comprises a peptide having the amino acid sequence set forth in any one of SEQ ID NO:4, SEQ ID NO:5, SEQ ID NO:6 and SEQ ID NO:7. Each possibility represents a separate embodiment of the present invention.

According to some exemplary embodiments, the present invention provides a pharmaceutical composition comprises at least one peptide conjugate having an amino acid sequence selected from the group consisting of SEQ ID NO:9, SEQ ID NO:10, SEQ ID NO:11, SEQ ID NO:12, SEQ ID NO:14, SEQ ID NO:15, SEQ ID NO:16 and SEQ ID NO:17 further comprising a therapeutically acceptable diluents or carrier. Each possibility represents a separate embodiment of the present invention.

Apart from other considerations, the fact that the novel active ingredients of the invention are peptides, peptide analogs or peptidomimetics, dictates that the formulation be suitable for delivery of these types of compounds. Although in general peptides are less suitable for oral administration due to susceptibility to digestion by gastric acids or intestinal enzymes, the compositions of the present invention may be administered orally due to the high activity observed for the stable D-stereomeric peptides of the invention. In addition, novel methods are being used in order to design and provide metabolically stable and oral bioavailable peptidomimetic analogs.

The pharmaceutical composition of this invention may be administered by any suitable means, such as topically, or parenterally including intranasal, subcutaneous, intramuscular, intravenous, intra-arterial, intraarticular, or intralesional administration. Ordinarily, intravenous (i.v.), intraarticular administration will be preferred.

The molecules of the present invention as active ingredients are dissolved, dispersed or admixed in a diluent or excipient that is pharmaceutically acceptable and compatible with the active ingredient as is well known. Suitable excipients are, for example, water, saline, phosphate buffered saline (PBS), dextrose, glycerol, ethanol, or the like and combinations thereof. Other suitable carriers are well known to those in the art. (See, for example, Ansel et al., 1990 and Gennaro, 1990). In addition, if desired, the composition can contain minor amounts of auxiliary substances such as wetting or emulsifying agents, pH buffering agents.

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants, for example polyethylene glycol, are generally known in the art.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration. For buccal administration, the compositions may take the form of tablets or lozenges formulated in conventional manner.

In one exemplary embodiment according to the present invention, the peptides are administered orally (e.g. as a syrup, capsule, or tablet). In certain embodiments, peptide delivery can be enhanced by the use of protective excipients. This is typically accomplished either by complexing the peptide with a composition to render it resistant to acidic and enzymatic hydrolysis or by packaging the peptide in an appropriately resistant carrier such as a liposome. Means of protecting peptides for oral delivery are well known in the art.

A tablet may be made by compression or molding, optionally with one or more accessory ingredients. Compressed tablets may be prepared by compressing in a suitable machine the active peptide(s) in a free-flowing form such as a powder or granules, optionally mixed with a binder, (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose), surface active or dispersing agent. Molded tablets may be made by molding in a suitable machine a mixture of the powdered peptide(s) moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile.

Syrup may be made by adding the active peptide(s) to a concentrated, aqueous solution of a sugar, for example, sucrose, to which may also be added any necessary ingredients. Such accessory ingredients may include flavorings, an agent to retard crystallization of the sugar or an agent to increase the solubility of any other ingredients, such as a polyhydric alcohol, for example, glycerol or sorbitol.

For administration by inhalation, the variants for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflators may be formulated containing a powder mix of the peptide and a suitable powder base such as lactose or starch.

Pharmaceutical compositions for parenteral administration include aqueous solutions of the active ingredients in water-soluble form. Additionally, suspensions of the active compounds may be prepared as appropriate oily injection suspensions. Suitable natural or synthetic carriers are well known in the art (Pillai et al., 2001. Curr Opin Chem Biol 5:447). Optionally, the suspension may also contain suitable stabilizers or agents, which increase the solubility of the compounds, to allow for the preparation of highly concentrated solutions. Alternatively, the active ingredient may be in powder form for reconstitution with a suitable vehicle, e.g., sterile, pyrogen-free water, before use.

The compounds of the present invention may also be formulated in rectal compositions such as suppositories or retention enemas, using, e.g., conventional suppository bases such as cocoa butter or other glycerides.

Elevated serum half-life can be maintained by the use of sustained-release protein "packaging" systems. Such sustained release systems are well known to those of skill in the art. In one exemplary embodiment, a biodegradable microsphere delivery system for proteins and peptides such as the ProLease® system (reviewed in Tracy M A. 1998. Biotechnol Prog 14:108) a dry powder composed of biodegradable polymeric microspheres containing the peptide in a polymer matrix that can be compounded as a dry formulation with or without other agents. Serum half-life can also be extended by conjugating the peptide or polypeptide of the invention to a moiety such as PEG using reagents and methods known to those with skill in the art.

The foregoing formulations and administration methods are intended to be illustrative and not limiting. It will be appreciated that, using the teaching provided herein, other suitable formulations and modes of administration can be readily devised.

Pharmaceutical compositions suitable for use in context of the present invention include compositions wherein the active ingredients are contained in an amount effective to achieve the intended purpose. More specifically, a therapeutically effective amount means an amount of a compound effective to prevent, delay, alleviate or ameliorate symptoms of a disease of the subject being treated. Determination of a therapeutically effective amount is well within the capability of those skilled in the art.

Toxicity and therapeutic efficacy of the peptides and peptide conjugates described herein can be determined by standard pharmaceutical procedures in cell cultures or experimental animals, e.g., by determining the $IC_{50}$ (the concentration which provides 50% inhibition as exemplified herein) and the $LD_{50}$ (lethal dose causing death in 50% of the tested animals) for a particular peptidic or peptidomimetic compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition (e.g. Fingl, et al., 1975, in "The Pharmacological Basis of Therapeutics", Ch. 1 p. 1).

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing physician, and all other relevant factors.

According to some embodiments of the invention, the therapeutically effective amount of the peptide, peptide conjugate, derivative or analog is a dosage in a range from about 0.1 µg/Kg body weight to about 20 mg/Kg body weight. According to certain exemplary embodiments, the dosage of the peptides or peptide conjugates according to the present invention is in a range from about 10 µg/Kg body weight to about 5 mg/Kg body weight.

It will be understood that dosage may be administered such that, for example, low dosage may be administered first, and subsequently higher dosages may be administered until an appropriate response is achieved. Also, the dosage of the composition can be administered to the subject in multiple administrations in the course of the treatment period in which a portion of the dosage is administered at each administration.

Without wishing to be bound by any theory or mechanism of action, the peptide, peptide conjugate, derivative or analog thereof is designed to interfere with VDAC1 protein-protein interactions. According to certain exemplary embodiments, the peptide, peptide conjugate, derivative or analog thereof is designed to inhibit interactions between VDAC1 protein and a mitochondrial anti-apoptosis protein.

The art discloses examples of peptides and analogs thereof designed to interfere with protein-protein interactions. For example, SAHB (stabilized a helix of Bcl-2 domains) is a helical, protease resistant, cell permeable peptidomimetic useful for activation of apoptosis in cancer cells (Walensky L D et al., 2004. Science. 305(5689):1466-1470). Another example is a peptidomimetic designed to mimic the protein-protein interactions of an apoptotic activator, SMAC (Li L et al, 2004. Science. 305(5689): 1471-1474).

In yet another aspect the present invention provides a method for treating a subject suffering from a disease associated with aberrant apoptosis and/or cell hyperproliferation, the method comprising administering to a subject in need thereof a pharmaceutical composition comprising a therapeutically effective amount of at least one peptide of 5-25 amino acids comprising a contiguous sequence derived from the N-terminal domain of VDAC1, comprising the GXXXG motif, wherein G is a glycine residue or a modified glycine residue or a conjugate thereof.

According to additional aspect, the present invention provides the use of at least one peptide of 5-25 amino acids comprising a contiguous sequence derived from the N-terminal domain of VDAC1, comprising the GXXXG motif, wherein G is a glycine residue or a conjugate thereof for the preparation of a medicament useful in treating a disease associated with aberrant apoptosis and/or cell hyperproliferation.

In some embodiments the disease is a cancerous disease including chemo- and radiotherapy-resistant cancer. According to certain typical embodiments, the disease associated with aberrant apoptosis is cancer. According to further typical embodiments, the cancer is selected from the group consisting of leukemia, hepatocellular carcinoma, pancreatic cancer, glioblastoma, cervical carcinoma, malignant melanoma, alveolar basal cell adenocarcinoma, bronchial veolar carcinoma, prostate cancer and breast cancer. Each possibility represents a separate embodiment of the present invention.

According to some exemplary embodiments, the cancer is chronic lymphocytic leukemia. According to other exemplary embodiments, the cancer is glioblastoma. According to yet additional exemplary embodiments, the cancer is prostate cancer.

Figures 6A, 6B:
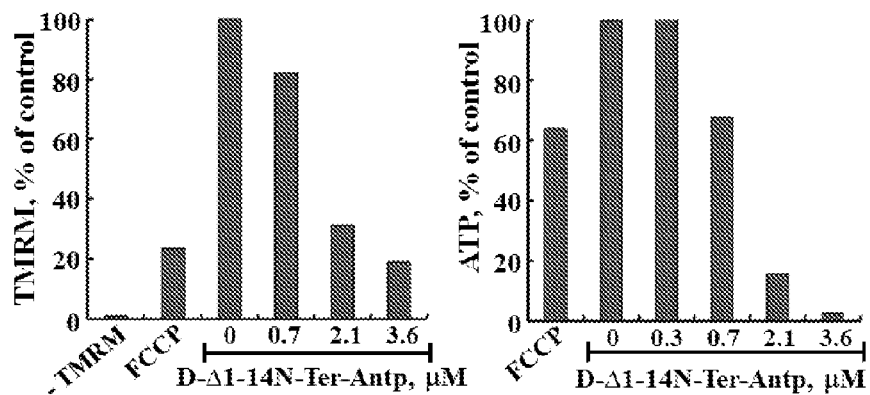
FIGS. 6A and 6B demonstrate that peptide D-Δ1-14N-Ter-Antp (SEQ ID NO:9) induces mitochondrial inner membrane depolarization and reduction of cellular ATP level in human glioblastoma U-87 cells. FCCP was use as a control for depolarization.
Figure 7:
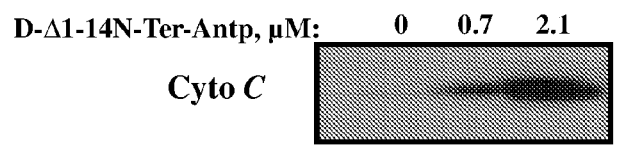
FIG. 7 shows that peptide D-Δ(1-14) N-Ter-Antp (SEQ ID NO:9) induces cytochrome c release in human glioblastoma U-87 cells. The release of cytochrome c from mitochondria to the cytosolic fraction was analyzed by immunoblotting.

Without wishing to be bound by any specific theory or mechanism of action, the present invention shows that the VDAC1-based short peptides have a double mode of action, affecting both cell energy production and inducing apoptosis (FIGS. 6-8). Altered energy metabolism, including enhanced aerobic glycolysis, is a fundamental phenotype of malignant tumors. Mitochondrial-bound HK is markedly elevated in highly glycolytic cancer cells, supporting aerobic glycolysis, critical for the stability of mitochondria and confers resistance to apoptosis. As exemplified herein, peptide D-Δ(1-14) N-Ter-Antp (SEQ ID NO:9) induces HK-1 detachment from HeLa cells (FIG. 9) and mitochondrial inner membrane depolarization and reduction of cellular ATP level in human glioblastoma U-87 cells (FIG. 6).

The mitochondrial pathway serves as an excellent target for apoptosis-inducing therapies for several reasons: mitochondria-directed agents are predicted to be effective at low concentrations, since only a fraction of a cell's mitochondria need to be involved for apoptosis to ensue; downstream effectors of mitochondrial apoptosis are present in all cell types, and seem to be conserved in tumor cells; and mitochondrial apoptosis induction is known to kill cells effectively.

The peptides of the invention and in particular peptides conjugated to cell-penetration moiety are highly suitable as therapeutic agents, owing to their specificity, rapid clearance from systemic circulation and ability to penetrate tumor tissue. In addition, the very short peptides of the invention are easy to synthesize and the cost of synthesis is relatively low. The short peptides of the invention further overcome the disadvantages of hitherto known peptides by being stable, and able to penetrate into the tumor once linked to a cell penetration moiety, particularly cell penetration peptides. The significant a specific cancer cell death induction by the peptide conjugates of the invention results from their multiple effects, including impairment of energy homeostasis and overcoming the protective and pro-survival actions taken by cancer cells.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Materials and Methods

Materials

7-Amino-actinomycin (7AAD), FCCP, leupeptine, phenylmethylsulfonyl fluoride (PMSF), propidium iodide (PI), tetramethylrhodamine methyl ester (TMRM), DAPI, 4',6-diamidino-2-phenylindole and trypan blue were purchased from Sigma (St. Louis, Mo.). Annexin-V was obtained from Alexis Biochemicals (Lausen, Switzerland). A CellTiter-Glo Luminescent Cell Viability assay kit was obtained from Promega (Madison, Wis.). Dulbecco's modified Eagle's medium (DMEM) and the supplements, fetal calf serum, L-glutamine and penicillin-streptomycin, were purchased from Biological Industries (Beit Haemek, Israel). Anti-VDAC1 mouse monoclonal antibodies were from Abcame. Anti-actin monoclonal antibodies were from Millipore (Billerica, Mass.). Monoclonal anti-CD5/CD19 and monoclonal anti-Cyto c antibodies were obtained from BD Bioscience (San Jose, Calif.). Anti-hexokinase-I antibodies, Anti-VDAC1 (ab15895) and Cy 2- and Cy 3-conjugated anti-mouse and anti-rabbit antibodies, respectively were obtained from Abcam. Horseradish peroxidase (HRP)-conjugated anti-mouse, anti-rabbit and anti-goat antibodies were from Promega.

Patients

Fifty-one CLL patients (26 women and 25 men) with a median age of 66 years were included in this study. CLL diagnosis was based on clinical examination, peripheral blood count and immuno-phenotyping (Table 1). The T cell-specific zeta-associated protein 70 (Zap 70) is an intracellular tyrosine kinase and serves to distinguish CLL subtypes, even though it is not considered to be a reliable prognostic marker. The expression of ZAP-70 and the co-expression of the T-cell antigen CD5 and B-cell surface antigens CD19 were analyzed in peripheral-blood samples from the patients with CLL using specific antibodies and flow cytometry. Positive (over 15%) and negative (less than 14%) signals are indicated by + and −, respectively, while ND indicates not determined About 13% of the tested samples were ZAP-positive. Patients received no treatment for the disease. Written informed consents were obtained from all patients, prior to sample collection, according to the Declaration of Helsinki. The ethic approval for the study was obtained from the local ethic committee of the research and was approved by the Soroka university medical center Advisory Committee on Ethics in Human Experimentation.

TABLE 1

Clinical characteristics of patients with B-CLL

| Identity | Age in years | Rai stage of disease | WBC $10^3/\mu l$ | Zap 70 | CD5/CD19 % | Gender |
|---|---|---|---|---|---|---|
| CLL 1 | 40 | 0 | 12 | ND | ND | M |
| CLL 2 | 73 | IV | 133 | | ND | M |
| CLL 3 | 72 | 0-I | 39 | − | ND | F |
| CLL 4 | 75 | I | 19.7 | − | ND | F |
| CLL 5 | 78 | 0 | 12.2 | −/+ | ND | F |
| CLL 6 | 83 | I | 16.7 | ND | ND | F |
| CLL 7 | 58 | IV | 57.6 | + | ND | F |
| CLL 8 | 64 | II | 40 | + | ND | F |
| CLL 9 | 56 | III | 56.8 | − | ND | M |
| CLL 10 | 62 | I | 15.9 | − | ND | F |
| CLL 11 | 62 | 0 | 28.8 | + | 75.7 | F |
| CLL 12 | 74 | I | 15 | − | 32.7 | M |
| CLL 13 | 57 | I | 18.8 | − | ND | M |
| CLL 14 | 83 | I | 20 | ND | 60.7 | M |
| CLL 15 | 83 | I | 29 | − | 58.3 | F |
| CLL 16 | 75 | I | 27 | ND | 74 | M |
| CLL 17 | 70 | III | 43 | − | 64.8 | F |
| CLL 18 | 64 | 0-I | 20 | − | 64.7 | M |
| CLL 19 | 56 | I | 36 | − | 13.4 | F |
| CLL 20 | 71 | 0-I | 12 | ND | 68.3 | M |
| CLL 21 | 56 | I | 40 | − | 77.2 | M |
| CLL 22 | 63 | 0 | 17.8 | + | 53 | F |
| CLL 23 | 52 | III | 147 | − | 78 | F |
| CLL 24 | 68 | 0 | 18 | ND | 50.8 | M |
| CLL 25 | 84 | I | 67 | − | 83 | M |
| CLL 26 | 68 | 0-I | 13.6 | ND | 8.5 | M |
| CLL 27 | 80 | 0 | 33.4 | ND | 62 | F |
| CLL 28 | 59 | 0 | 13.4 | − | 46.9 | M |
| CLL 29 | 73 | I | 17 | ND | 60.6 | M |
| CLL 30 | 80 | II | 71 | ND | 50.4 | F |
| CLL 31 | 61 | 0 | 7 | − | 38.1 | M |
| CLL 32 | 75 | I | 31 | − | 67 | F |
| CLL 33 | 75 | II-III | 27.2 | ND | 81.6 | M |
| CLL 34 | 52 | III | 126 | −/+ | 95 | F |
| CLL 35 | 67 | IV | 58 | − | 78 | M |
| CLL 36 | 64 | IV | 64 | + | 90.1 | F |
| CLL 37 | 76 | 0 | 28 | + | 40.5 | F |
| CLL 38 | 80 | I | 23 | − | 74 | M |
| CLL 39 | 49 | I | 13 | − | 13 | F |
| CLL 40 | 72 | 0-I | 14.8 | ND | ND | M |
| CLL 41 | 75 | I | 15 | − | 13 | F |
| CLL 42 | 85 | I | 26 | ND | 81 | M |
| CLL 43 | 71 | II | 48 | − | 84 | F |
| CLL 44 | 64 | 0 | 15.7 | − | 18 | F |
| CLL 45 | 73 | II | 22.7 | − | ND | F |
| CLL 46 | 83 | I | 29.8 | − | 55 | F |
| CLL 47 | 78 | IV | 26.6 | ND | 65 | F |
| CLL 48 | 84 | 0 | 22 | − | 78 | F |
| CLL 49 | 92 | 0 | 9 | ND | ND | M |
| CLL 50 | 61 | IV | 40 | ND | ND | M |
| CLL 51 | 63 | IV | 64 | − | ND | M |

Isolation of PBMCs and Cell Culture

PBMCs were isolated from venous blood of the CLL patients by Ficoll-Paque PLUS (GE Healthcare, Israel) density gradient centrifugation, as follows. Venous blood (10-20 ml) was drawn from CLL patients with satisfying diagnostic criteria for CLL or from normal adult donors. Blood was collected into heparin tubes and was diluted 1:1 with balance solution composed of two stock solutions, A (1% D-glucose, 50 mM CaCl2, 0.98 mM MgCl2, 5.4 mM KCl and 0.145 M Tris-HCl, pH 7.6) and B (0.14 M NaCl) in a 1:9 ratio. The resulting mix was carefully layered on Ficoll-Paque Plus (10 ml of diluted blood:15 ml Ficoll) in 50 ml conical tubes. The tubes were centrifuged at 400×g (with minimal acceleration and deceleration) and 18-20° C. for 40 min. The fine layer of mononuclear cells was transferred to a new centrifuge tube, washed 3 times with balance solution and resuspended in culture medium appropriate to the application. Cells were counted by a Countess Automated Cell Counter (Invitrogen).

The proportion of cancerous B cells out of the total PBMC pool was analyzed by detection of CD19/CD5 double positive cells in a flow cytometer (Beckton-Dickinson, San Jose, Calif.) using specific antibodies. PBMCs isolated from CLL patients were used freshly for the different experiments or were maintained up to one week in DMEM supplemented with 10% fetal calf serum, 2 mM L-glutamine, 100 U/ml penicillin, 100 μg/ml streptomycin, 1 mM sodium pyruvate, non-essential amino acids, 10 mM Hepes and 11 μM mercaptoethanol (all from Biological Industries) in a humidified chamber of 95% air, 5% $CO_2$ at 37° C. Aliquots of the PBMCs in 90% FCS, 10% dimethyl sulfoxide (DMSO) at concentration of $2.5×10^7$ cells/ml were cryo-preserved in liquid nitrogen. After thawing, the PBMCs were maintained as described above. No significant differences in the results obtained from assays conducted using fresh cells, tissue culture-maintained cells or frozen cells were noted.

MEC-1, MO1043 and T-Rex-293 cells were grown in DMEM supplemented with 10% FCS, 2 mM L-glutamine, 1000 U/ml penicillin and 1 mg/ml streptomycin, U-87, C6 and PC3 were maintained in RPMI 1640 supplemented with 10-20% FCS, 2 mM L-glutamine, 1000 U/ml penicillin and 1 mg/ml streptomycin. All cells were maintained in a humidified atmosphere with 5% $CO_2$ at 37° C.

Peptides

Custom VDAC-1-based peptides were synthesized by GL Biochem (Shanghai, China) to >85% purity. Synthesized peptides based on VDAC1 N-terminal domain are listed in Table 2. Previously disclosed VDAC1 based peptide was used in the course of the present invention as a reference to evaluate the activity of the novel short peptides. The peptide, designated Tf-D-LP4 is a conjugate of peptide LP4 comprising the amino acid sequence of positions 199-216 of human VDAC1 protein (SEQ ID NO:18), having the amino acids sequence set forth in SEQ ID NO:19, with the cell penetrating peptide Tf (SEQ ID NO:13). The conjugate has the amino acids sequence set forth in SEQ ID NO:20).

The peptides were dissolved in 20% DMSO and concentrations were determined using absorbance at 280 nm and the specific molar excitation coefficient, as calculated based on amino acid composition. For all experiments, the final concentration of DMSO in control and peptide containing samples was up to 0.5%.

TABLE 2

Peptides synthesized based on the VDAC1 N-terminal domain

| Peptide designation | Peptide Sequence | SEQ ID NO |
|---|---|---|
| N-Ter-Antp | MAVPPTYADLGKSARDVFTKGYGFGL RQIKIWFQNRRMKWKK | 21 |
| Δ(1-18) N-Ter-Antp | TKGYGFGL RQIKIWFQNRRMKWKK | 10 |
| D-Δ(1-18) N-Ter-Antp | ALL D-TKGYGFGL RQIKIWFQNRRMKWKK | 10 |
| Δ(1-14) N-Ter-Antp | RDVFTKGYGFGL RQIKIWFQNRRMKWKK | 9 |
| D-Δ(1-14) N-Ter-Antp | ALL D-RDVFTKGYGFGL RQIKIWFQNRRMKWKK | 9 |
| Δ(1-10) N-Ter-Antp | GKSARDVFTKGYGFGL RQIKIWFQNRRMKWKK | 11 |
| D-Δ(1-10) N-Ter-Antp | ALL D-GKSARDVFTKGYGFGL RQIKIWFQNRRMKWKK | 11 |
| Δ(1-4) N-Ter-Antp | PTYADLGKSARDVFTKGYGFGL RQIKIWFQNRRMKWKK | 12 |
| D-Δ(1-4) N-Ter-Antp | ALL D-PTYADLGKSARDVFTKGYGFGL RQIKIWFQNRRMKWKK | 12 |
| Δ(21-26) N-Ter-Antp | MAVPPTYADLGKSARDVFTK RQIKIWFQNRRMKWKK | 22 |

Determination of Cell Viability

Cell viability was analyzed by assaying trypan blue (0.2%) exclusion, as counted by a Countess Automated Cell Counter (Invitrogen).

Cell Treatment with VDAC1-Based Peptides and Cell Death Analysis.

PBMCs ($4 \times 10^5$ or $8 \times 10^5$ cells/sample) were incubated in 200 µl serum-free medium with the examined peptide for 90 min at room temperature and centrifuged (500×g, 5 min) Cell death was analyzed by PI staining and flow cytometer (Beckton-Dickinson) and BD Cell Quest Pro software. Apoptotic cell death was also analyzed by PI and annexin V-FITC staining (Zaid H et al. 2005. 12:751-760), and by acridine orange and ethidium bromide staining and confocal microscopy (Olympus 1×81).

ATP Quantification

U-87 cells were seeded in 96-well plates ($2 \times 10^6$/ml), incubated for 3 h with the indicated concentrations of D-Δ1-14N-Ter-Antp (SEQ ID NO:9), washed twice with PBS and incubated with the CellTiter-Glo reagent (Promega). Luminescence was recorded using an Infinite M1000 microplate reader (Tecan Trading, Mannedorf, Switzerland).

Mitochondrial Membrane Potential Analysis

U-87 cells were incubated with the indicated concentrations of D-Δ1-14N-Ter-Antp (SEQ ID NO:9), washed with PBS, incubated with or without the potentiometric fluorescent dye TMRM (200 nM, 20 min), washed with PBS and subjected to FACS analysis. FCCP, allowing for Δψ dissipation, served as a control.

Cytochrome c Release

Release of cytochrome c (Cyt c) from mitochondria to the cytosol was measured by immunoblots. Cells were incubated for 5 h with the indicated concentration of the peptide, harvested, washed twice with PBS and gently resuspended in ice-cold buffer (100 mM KCl, 2.5 mM MgCl2, 250 mM sucrose, 20 mM HEPES/KOH pH 7.5, 0.2 mMEDTA, 1 mM dithiothreitol, 1 µg/ml leupeptin, 5 µg/ml cytochalasin B and 0.1 mM phenylmethylsulfonyl fluoride) containing 0.025% digitonin and incubated for 10 min on ice. Samples were centrifuged at 10,000 g at 4° C. for 5 min to obtain the supernatants (cytosolic extracts free of mitochondria) and the pellets (fraction that contains mitochondria). The supernatants were analyzed by SDS-PAGE and immunoprobed using anti-Cyto c antibodies (1:2000, BD Pharmingen™ Cat #556433), and then with secondary horseradish peroxidase (HRP)-conjugated anti-mouse antibodies.

Example 1

Optimization of VDAC1-N-Terminal Domain Derived Peptides

Figure 2:
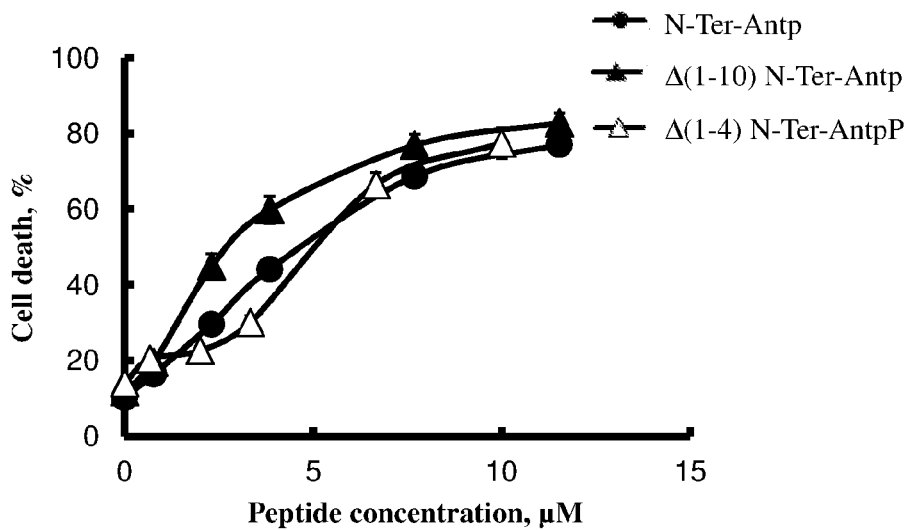
FIG. 2 shows that short peptides based on the amino acid sequence of VDAC1 N-terminal domain are active in inducing death of MEC-1 cells. Peptide N-Ter-Antp is described in FIG. 1 above. Peptide Δ(1-10) N-Ter-Antp: amino acids 11-26 of the VDAC1 N-terminal domain with Antp (SEQ ID NO:11). Peptide Δ(1-4) N-Ter-Antp: amino acids 5-26 of the VDAC1 N-terminal domain with Antp (SEQ ID NO:12). Data represent mean values, n=3.
Figure 4:
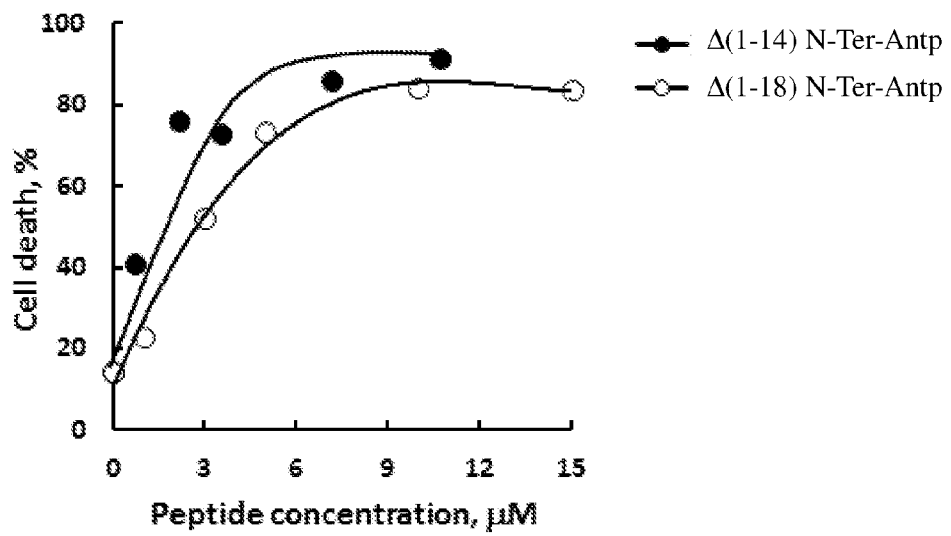
FIG. 4 shows that peptide based on the amino acid sequence of VDAC1 N-terminal domain as short as 8 amino acids is active in inducing death of cells established from the peripheral blood of a patient with CLL (MO1043 cells). Peptide Δ(1-18) N-Ter-Antp: amino acids 19-26 of the VDAC1 N-terminal domain with Antp (SEQ ID NO:10).

To optimize the VDAC1 N-terminal derived peptides with respect to stability, length and specific targeting to cancer cells, several versions of these peptides were designed and tested for their efficacy in inducing the death of CLL-derived lymphocytes and MEC-1 cells (Table 3). Cells were incubated for 90 min with increasing concentrations of the indicated peptide and death was analyzed by PI staining and FACS as described hereinabove. As is clearly shown in FIG. 1 (and Table 3), deleting 6 residues from the C-terminus of the peptide, including the GXXXG motif, yielded a non-active peptide (peptide Δ(21-26) N-Ter-Antp, SEQ ID NO:22). However, shortening the VDAC1-N-terminal domain from its N-terminus by 4 amino acids (peptide Δ(1-4) N-Ter-Antp, SEQ ID NO:12), or by 11 amino acids (peptide Δ(1-10) N-Ter-Antp, SEQ ID NO:11) did not significantly modified the cell-death induction activity of the peptides (FIG. 2). Moreover, peptides as short as 8 and 12 amino acids, lacking the 1-18 or 1-14 N-terminus amino acids of the VDAC1 N-terminal domain respectively, and linked to the Antp sequence as a CPP (Δ(1-18) N-Ter-Antp, SEQ ID NO:10; Δ(1-14) N-Ter-Antp, SEQ ID NO:9), were more active in inducing the death of cells established from the peripheral blood of a patient with CLL (MO1043 cells) or of MEC-1 cells compared to the previously disclosed peptide derived from VDAC1 N-terminal domain comprising 26 amino acids (N-Ter-Antp having SEQ IS NO:21, see Table 3; FIG. 4).

Shorter peptides are expected to be less prone to protease activity, as the sequences recognized by the protease may be absent and/or are too short to initiate proteolysis, and thus more stable. Additional protection to enzymatic degradation may be obtained by synthesizing peptides that comprise at least part of the amino acids in their D-configuration. As exemplified herein (Table 3 and FIG. 3), the short peptides of the invention comprising D-amino acids were not only as active as the peptides comprising the native amino acids, but showed higher inhibiting activity (Table 3).

These results demonstrate that the peptides of the invention that are very short and comprising D-amino acids keeps the ability to induce cell apoptosis and cell death, and are thus highly suitable for use as a therapeutic compounds.

TABLE 3

Induction of cell death by truncated
N-terminal domain VDAC1 derived peptides

| Peptide Designation | IC$_{50}$, µM | |
|---|---|---|
| | CLL | MEC-1 |
| N-Ter-Antp (SEQ ID NO: 21) | 3.2 ± 0.5 (n = 6) | 4.2 ± 0.2 (n = 12) |
| Δ(21-26) N-Ter-Antp (SEQ ID NO: 22) | >12.5 (n = 3) | >12.5 (n = 3) |
| Δ(1-4) N-Ter-Antp (SEQ ID NO: 12) | ND | 4.2 ± 0.2 (n = 4) |
| Δ(1-10) N-Ter-Antp (SEQ ID NO: 11) | ND | 2.5 ± 0.2 (n = 7) |
| D-Δ(1-10) N-Ter-Antp (SEQ ID NO: 11) | ND | 1.9 ± 0.2 (n = 7) |
| Δ(1-14) N-Ter-Antp (SEQ ID NO: 9) | 2.2 ± 0.2 (n = 3) | 3.3 ± 0.2 (n = 7) |
| D-Δ(1-14) N-Ter-Antp (SEQ ID NO: 9) | 1.3 ± 0.1 (n = 2) | 2.1 ± 0.3 (n = 3) |
| D-Δ(1-18) N-Ter-Antp (SEQ ID NO: 10) | 2.5 ± 0.1* (n - 3) | |

*Inhibiting MO1043 cells;
ND- Not Detected

Example 2

The Short Peptides Show Wide Range of Activity

Figures 3A, 3B, 3C:
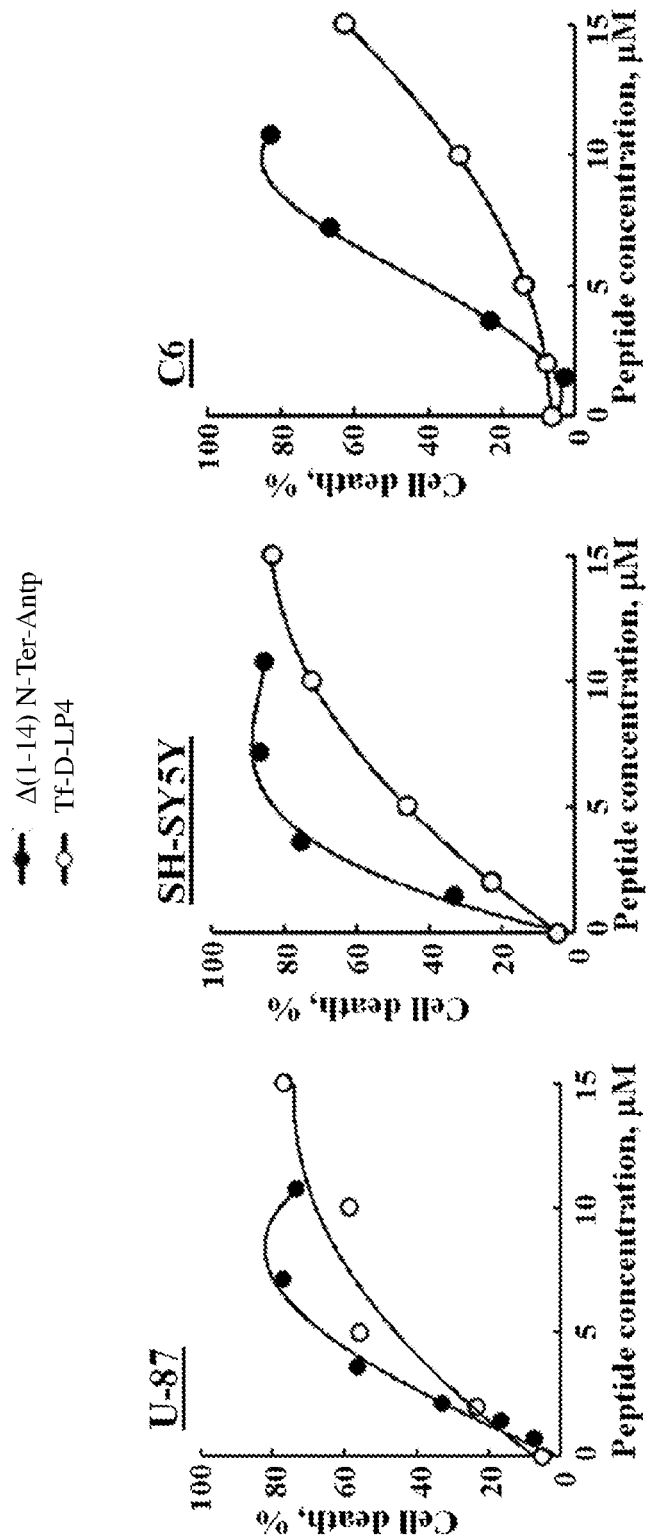
FIGS. 3A, 3B and 3C show that peptide D-Δ1-14N-Ter-Antp effectively induces cell death of brain tumor-derived cell.

The efficacy of the peptide comprising amino acids 11-26 of the N-terminal domain of VDAC1, synthesized with D-amino acids (all D-stereomeric peptide) conjugated to the Antp sequence also synthesized from D-amino acids as a CPP (D-Δ(1-14) N-Ter-Antp, SEQ ID NO:9) was further examined for its activity of inducing cell death with brain tumor derived cell lines. Human primary glioblastoma cells (U-87), human neuroblastoma cells (SH-SY5Y) and rat glioblastoma cells (C6) were incubated (4×10$^5$ cells) for 6 h in a serum-free-medium containing different concentrations of D-Δ1-14N-Ter-Antp (SEQ ID NO:9). The previously disclosed LP4 peptide conjugated to Tf (Tf-D-LP4 peptide, SEQ ID NO:20) was used as a reference of activity. At the end of the incubation time the cells were stained with PI and the level of cell death, reflected by the percentage of PI-positive cells, was determined by flow cytometry. FIG. 3 shows that incubation of all cell line types with peptide D-Δ(1-14) N-Ter-Antp resulted in significant cell death. IC$_{50}$ for D-Δ1-14N-Ter-Antp in U87, SH-SY5Y and C6 cells was 3.75, 2.05 and 5.3 µM, respectively.

Figure 5:
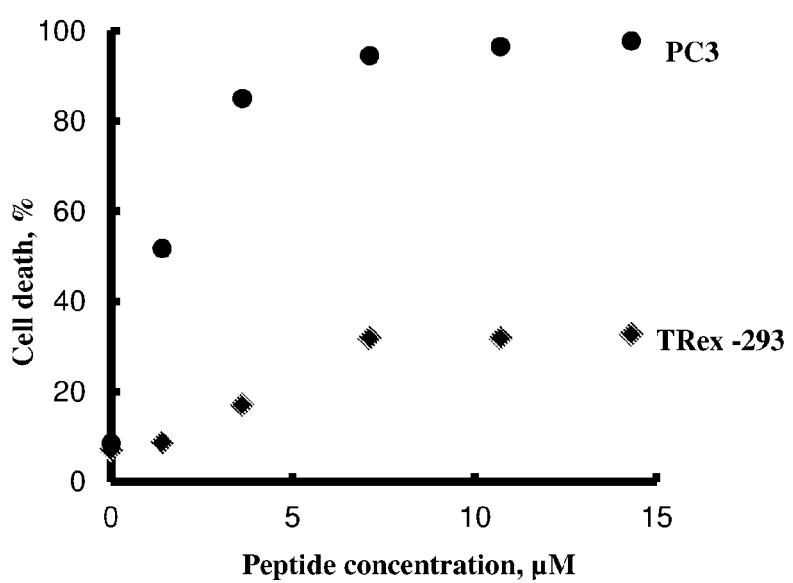
FIG. 5 shows that peptide D-Δ1-14N-Ter-Antp (SEQ ID NO:9) selectively induce cell death of prostate cancer cell lines PC-3. Reduced effect was observed for the non-malignant and T-Rex-293 cells. Data represent mean values, n=3.

It was previously disclosed that peptide Antp-LP4 (SEQ ID NO:23) derived from another part of VDAC1, selectively induce cell death of cancerous cells co-expressing the cell surface markers CD19 and CD5 (U.S. Pat. No. 8,648,045) as well as other cancer cells as HeLa. The present invention now shows that incubation of the short peptide D-Δ(1-14) N-Ter-Antp with control cells (T-Rex-293, primary human embryonal kidney cell line resulted in some induction of cell death, while incubation of the peptide with human prostate cancer cell lines (PC3) resulted in a dramatic cell death (FIG. 5).

Example 3

Effect of Peptide D-Δ(1-14) N-Ter-Antp on Mitochondria Membrane Potential and Cellular ATP Level VDAC1 is a key component in regulating the energy production of the cell. It is known that cancer cells are characterized by elevated energy demand. The effects of D-Δ(1-14) N-Ter-Antp on the mitochondrial inner membrane polarization and cellular ATP level were examined using glioblastoma U-87 cells. U-87 cells were incubated for 3 h with the various concentrations of D-Δ1-14N-Ter-Antp or with FCCP (10 µM, control for depolarization) for 1 h. FIG. 6 shows that D-Δ(1-14) N-Ter-Antp induced mitochondrial inner membrane depolarization (FIG. 6A) and almost complete reduction of cellular ATP level (FIG. 6B).

Example 4

Pro-Apoptotic Activity of D-Δ(1-14) N-Ter-Antp

Mitochondria play an important role in the regulation of apoptotic cell death. The release of apoptogenic intermediates such as cytochrome c from the intermembranal space into the cytoplasm of a cell initiates a cascade of caspase activation that executes the cell death program.

The effect of D-Δ(1-14) N-Ter-Antp on apoptosis was examined in the glioblastoma cell line U-87. U-87 cells were incubated with and without the peptide, treated with digitonin (0.02%) and the release of cytochrome c from mitochondria to the cytosolic fraction was analyzed by immunoblotting. As is clearly shown in FIG. 7, the release of cytochrome c from the mitochondria was significantly induced by peptide D-Δ(1-14) N-Ter-Antp in a concentration-depended manner.

Figure 8A:
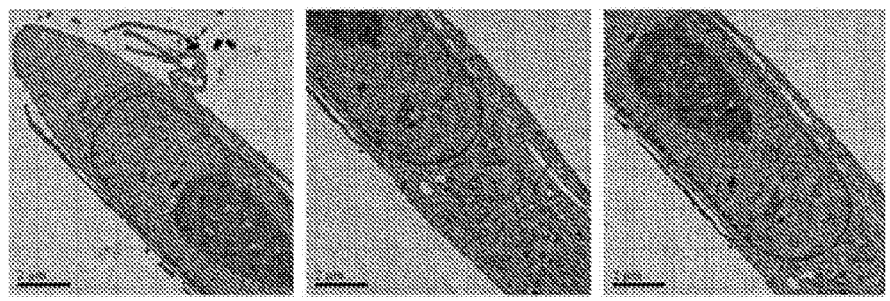
FIGS. 8A and 8B show transmission electron microscopy (TEM) visualization of apoptosis induced by peptide D-Δ(1-14) N-Ter-Antp (SEQ ID NO:9) on human glioblastoma U-87 cells.
Figure 8B:
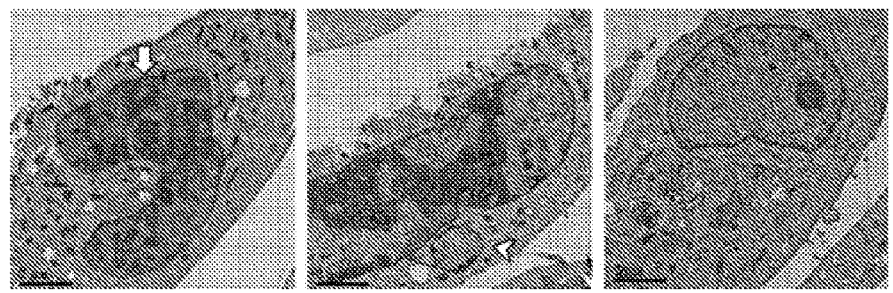

Visualization of apoptotic cell death of U-87 cells induced by D-Δ1-14N-Ter-Antp is presented in FIG. 8. Representative images of transmission electron microscopy (TEM) of untreated cells (FIG. 8A) or cells treated with 2.8 µM of D-Δ1-14N-Ter-Antp (FIG. 8B) are shown. In the peptide-treated cells, typical morphologic changes associated with apoptosis, such as condensation of nucleus (arrows), DNA fragmentation (arrowheads), were noted.

Example 5

D(Δ1-14) N-Terminal-Antp Induces Detachment of Mitochondria-Bound Hexokinase 1 (HK-1)

To visualize HK detachment induced by the D-Δ(1-14) N-terminal-Antp peptide, HeLa cells (3×10$^5$) were grown on Poly-D-Lysine (PDL)-coated coverslips in a 60 mm dish and transfected with pEGFP-HK-I or with plasmid pEGFP. HK-I-GFP fusion protein, in which GFP was connected to the HK-I C-terminal (pEGFP-HK-I), was constructed using an EcoR1 restriction site to introduce GFP into the 3' (at the stop codon) of HK1 in plasmid pcDNA3.1 by site-directed mutagenesis with overlapping PCR amplification, using the following primers: 5'-CCCTTCGATCGCCGGAATTCCA-GGATCCTCCCAGCC-3; (forward, SEQ ID NO:24) and 5'-GGCTGGGAGGATCCTGGAATTCCGGCGATC-GAAGGG-3; (reverse, SEQ ID NO:25).

Figure 9:
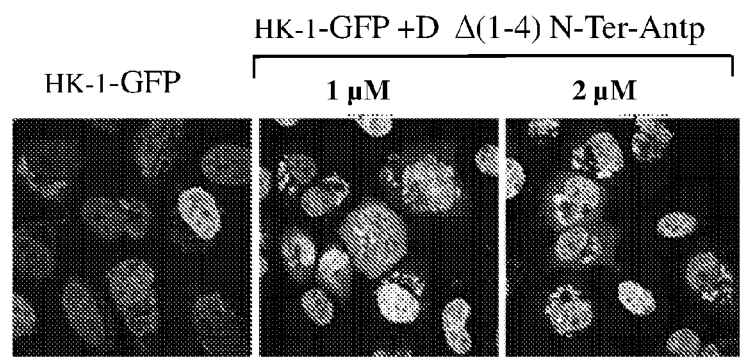
FIG. 9 demonstrates that peptide D-Δ(1-14) N-Ter-Antp (SEQ ID NO:9) induces HK-1 detachment from HeLa cells. Cells expressing HK-1-GFP fusion protein were incubated with a serum-free medium containing 0.4% DMSO or with the indicated concentration of D-Δ(1-14) N-Ter-Antp peptide. GFP fluorescence was detected using confocal microscopy (Olympus 1×81).

After 48 h, cells were incubated for 6 h with a serum-free medium containing 0.4% DMSO or with the indicated concentration of D-Δ(1-14) N-Ter-Antp peptide. Cells were washed with PBS, fixed for 20 min with 4% paraformaldehyde prepared in PBS, rinsed for 30 min in PBS and cell imaging was carried out by confocal microscopy (Olympus 1×81). FIG. 9 shows that in HeLa cells expressing HK-1 linked to the fluorescent peptide GFP, a punctuated distribution is observed, indicating the HK-1 is attached to the mitochondria. In the presence of peptide D(Δ1-14) N-terminal-Antp, however, diffusion of HK-1-GFP out into the cytosol is observed, suggesting its detachment from the mitochondria.

Example 6

In Vivo Effect of D-Δ1-14N-Ter-Antp

Figure 10A:
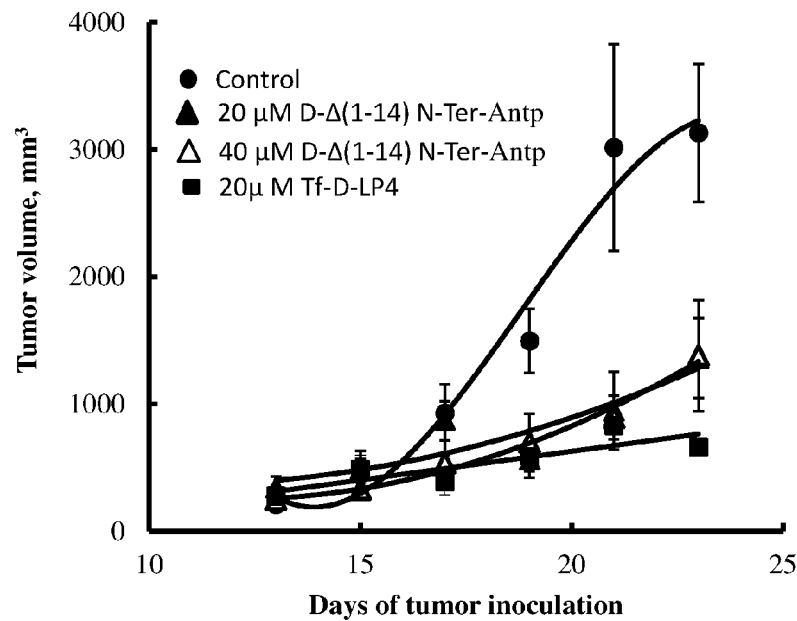
FIGS. 10A and 10B demonstrate that peptide D-Δ(1-14) N-Ter-Antp (SEQ ID NO:9) inhibits tumor growth in glioblastoma xenografts. Xenografts were injected with 0.26% DMSO as a control or with different concentrations of peptide D-Δ(1-14) N-Ter-Antp. The previously disclosed peptide Tf-D-LP4 (SEQ ID NO:20) was used as a reference of activity.
Figure 10B:
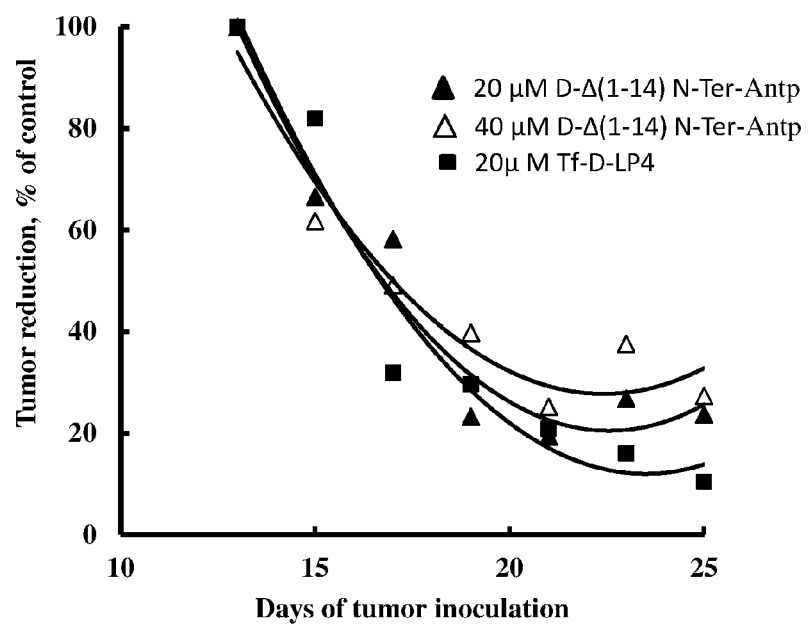

U87 cells were inoculated into male nude mice ($7 \times 10^6$ cells/mouse). Tumor volumes were monitored (using a digital caliper) and on day 11, the mice were divided into 3 groups (5 mice per group), with each mouse containing a tumor with a volume between 100-200 mm$^3$ and similar average volumes measured per group. The four mice groups were subjected to the following treatments: Xenografts were injected with 0.26% DMSO (control), with D-Δ1-14N-Ter-Antp (10 µl of 20 or 40 µM solutions) or with the previously disclosed Tf-LP4 peptide (10 µl of a 20 µM solution). FIG. 10A shows the xenograft size measured on the indicated days. FIG. 10B shows the decrease in tumor size of the treated tumors relative to the untreated tumors (% of decrease). As is clearly shown, peptide D-Δ1-14N-Ter-Antp significantly reduced the tumor size. These results demonstrate that the short peptides of the invention are active in vivo, similarly to the previously disclosed LP4 protein conjugated to Tf as a CPP (Tf-D-LP4).

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

What is claimed is:

1. A peptide conjugate which consists of the amino acid sequence set forth in any one of SEQ ID NO: 9 and SEQ ID NO: 10, wherein the amino acids of the amino acid sequence are selected from D-amino acids, L-amino acids, or a combination of D-amino acids and L-amino acids.

2. The peptide conjugate of claim 1, which is a D-L stereomeric peptide, wherein the amino acid sequence of the peptide conjugate consists of a combination of both D- and L-amino acids.

3. The peptide conjugate of claim 1, which is a D-stereomeric conjugate comprising which consists of only D-amino acids.

4. A pharmaceutical composition comprising the peptide conjugate of claim 1 and a therapeutically acceptable diluent or carrier.

5. The pharmaceutical composition of claim 4, wherein the peptide conjugate is a D-stereomeric peptide, which consists of only D-amino acids.

6. A method for treating a subject suffering from a disease associated with aberrant apoptosis and/or cell hyperproliferation, the method comprising administering to a subject in need thereof a pharmaceutical composition according to claim 4, wherein the disease is selected from the group consisting of leukemia, chronic lymphocytic leukemia (CLL), hepatocellular carcinoma, pancreatic cancer, glioblastoma, cervical carcinoma, malignant melanoma, alveolar basal cell adenocarcinoma, bronchial veolar carcinoma, prostate cancer and breast cancer.

7. The method of claim 6, wherein the disease is selected from the group consisting of chronic lymphocytic leukemia (CLL), glioblastoma and prostate cancer.

8. A method of inducing cancer cell death comprising applying to cancer cells at least one peptide conjugate according to claim 1, wherein the cancer cells are selected from the group consisting of leukemia cells, hepatocellular carcinoma cells, pancreatic cancer cells, glioblastoma cells, cervical carcinoma cells, malignant melanoma cells, alveolar basal cell adenocarcinoma cells, bronchial veolar carcinoma cells, prostate cancer cells and breast cancer cells.

* * * * *

UNITED STATES PATENT AND TRADEMARK OFFICE
CERTIFICATE OF CORRECTION

PATENT NO.       : 9,758,559 B2
APPLICATION NO.  : 14/907445
DATED            : September 12, 2017
INVENTOR(S)      : Shoshan-Barmatz It is certified that error appears in the above-identified patent and that said Letters Patent is hereby corrected as shown below:

On the Title Page

Page 2, Item (56) References Cited, OTHER PUBLICATIONS:
Arbel and Shoshan-Barrnatz reference, delete "Shoshan-Barrnatz" and insert -- Shoshan-Barmatz --;
Bourgeron et al. reference, delete "lymprioblastoid" and insert -- lymphoblastoid --;
Colonbini reference, delete "Colonbini" and insert -- Colombini --; and delete "beween" and insert -- between --;
Prezrna et al. reference, delete "Prezrna" and insert -- Prezma --;
Sapra and Alien reference, delete "Alien" and insert -- Allen --;
Shoshan-Barmaz et al. reference, delete "Shoshan-Barmaz" and insert -- Shoshan-Barmatz --; and
Sugiyama et al. reference, delete "mitrochondrial" and insert -- mitochondrial --.
Page 3, Item (56) References Cited, OTHER PUBLICATIONS:
Zheng et al. reference, delete "Oncoaene" and insert -- Oncogene --; and
Kayser H. et al. reference, delete "vdaci_human" and insert -- vdac1_human --.

In the Claims

Column 39:
Line 22 (Claim 3, Line 2), delete "comprising".

Signed and Sealed this
Twenty-fourth Day of October, 2017

Joseph Matal
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 25

<210> SEQ ID NO 1
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 1

Met Ala Val Pro Pro Thr Tyr Ala Asp Leu Gly Lys Ser Ala Arg Asp
1               5                   10                  15

Val Phe Thr Lys Gly Tyr Gly Phe Gly Leu
            20                  25

<210> SEQ ID NO 2
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(4)
<223> OTHER INFORMATION: Xaa can be any amino acid

<400> SEQUENCE: 2

Gly Xaa Xaa Xaa Gly
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Peptide
```

```
<400> SEQUENCE: 3

Gly Tyr Gly Phe Gly
1               5

<210> SEQ ID NO 4
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 4

Arg Asp Val Phe Thr Lys Gly Tyr Gly Phe Gly Leu
1               5                   10

<210> SEQ ID NO 5
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 5

Thr Lys Gly Tyr Gly Phe Gly Leu
1               5

<210> SEQ ID NO 6
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 6

Gly Lys Ser Ala Arg Asp Val Phe Thr Lys Gly Tyr Gly Phe Gly Leu
1               5                   10                  15

<210> SEQ ID NO 7
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 7

Pro Thr Tyr Ala Asp Leu Gly Lys Ser Ala Arg Asp Val Phe Thr Lys
1               5                   10                  15

Gly Tyr Gly Phe Gly Leu
            20

<210> SEQ ID NO 8
<211> LENGTH: 16
<212> TYPE: PRT
<213> ORGANISM: Artificial Sequence
<220> FEATURE:
<223> OTHER INFORMATION: Drosophila antennapedia (Antp) domain

<400> SEQUENCE: 8

Arg Gln Ile Lys Ile Trp Phe Gln Asn Arg Arg Met Lys Trp Lys Lys
1               5                   10                  15

<210> SEQ ID NO 9
<211> LENGTH: 28
<212> TYPE: PRT
<213> ORGANISM: Artificial Sequence
```

-continued

```
<220> FEATURE:
<223> OTHER INFORMATION: Synthetic Peptide

<400> SEQUENCE: 9

Arg Asp Val Phe Thr Lys Gly Tyr Gly Phe Gly Leu Arg Gln Ile Lys
1               5                   10                  15
Ile Trp Phe Gln Asn Arg Arg Met Lys Trp Lys Lys
            20                  25

<210> SEQ ID NO 10
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 10

Thr Lys Gly Tyr Gly Phe Gly Leu Arg Gln Ile Lys Ile Trp Phe Gln
1               5                   10                  15
Asn Arg Arg Met Lys Trp Lys Lys
            20

<210> SEQ ID NO 11
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 11

Gly Lys Ser Ala Arg Asp Val Phe Thr Lys Gly Tyr Gly Phe Gly Leu
1               5                   10                  15
Arg Gln Ile Lys Ile Trp Phe Gln Asn Arg Arg Met Lys Trp Lys Lys
            20                  25                  30

<210> SEQ ID NO 12
<211> LENGTH: 38
<212> TYPE: PRT
<213> ORGANISM: Artificial Sequence
<220> FEATURE:
<223> OTHER INFORMATION: Synthetic Peptide

<400> SEQUENCE: 12

Pro Thr Tyr Ala Asp Leu Gly Lys Ser Ala Arg Asp Val Phe Thr Lys
1               5                   10                  15
Gly Tyr Gly Phe Gly Leu Arg Gln Ile Lys Ile Trp Phe Gln Asn Arg
            20                  25                  30
Arg Met Lys Trp Lys Lys
        35

<210> SEQ ID NO 13
<211> LENGTH: 7
<212> TYPE: PRT
<213> ORGANISM: Artificial Sequence
<220> FEATURE:
<223> OTHER INFORMATION: TIR domain fragment

<400> SEQUENCE: 13

His Ala Ile Tyr Pro Arg His
1               5

<210> SEQ ID NO 14
<211> LENGTH: 19
<212> TYPE: PRT
```

<213> ORGANISM: Artificial Sequence
<220> FEATURE:
<223> OTHER INFORMATION: Synthetic Peptide

<400> SEQUENCE: 14

Arg Asp Val Phe Thr Lys Gly Tyr Gly Phe Gly Leu His Ala Ile Tyr
1               5                   10                  15

Pro Arg His

<210> SEQ ID NO 15
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 15

Thr Lys Gly Tyr Gly Phe Gly Leu His Ala Ile Tyr Pro Arg His
1               5                   10                  15

<210> SEQ ID NO 16
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 16

Gly Lys Ser Ala Arg Asp Val Phe Thr Lys Gly Tyr Gly Phe Gly Leu
1               5                   10                  15

His Ala Ile Tyr Pro Arg His
            20

<210> SEQ ID NO 17
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 17

Pro Thr Tyr Ala Asp Leu Gly Lys Ser Ala Arg Asp Val Phe Thr Lys
1               5                   10                  15

Gly Tyr Gly Phe Gly Leu His Ala Ile Tyr Pro Arg His
            20                  25

<210> SEQ ID NO 18
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 18

Lys Lys Leu Glu Thr Ala Val Asn Leu Ala Trp Thr Ala Gly Asn Ser
1               5                   10                  15

Asn

<210> SEQ ID NO 19
<211> LENGTH: 34
<212> TYPE: PRT
<213> ORGANISM: Artificial Sequence
<220> FEATURE:
<223> OTHER INFORMATION: Synthetic Peptide

```
<400> SEQUENCE: 19

His Ala Ile Tyr Pro Arg His Ser Trp Thr Trp Glu Lys Lys Leu Glu
1               5                   10                  15

Thr Ala Val Asn Leu Ala Trp Thr Ala Gly Asn Ser Asn Lys Trp Thr
            20                  25                  30

Trp Lys

<210> SEQ ID NO 20
<211> LENGTH: 42
<212> TYPE: PRT
<213> ORGANISM: Artificial Sequence
<220> FEATURE:
<223> OTHER INFORMATION: Synthetic Peptide

<400> SEQUENCE: 20

Met Ala Val Pro Pro Thr Tyr Ala Asp Leu Gly Lys Ser Ala Arg Asp
1               5                   10                  15

Val Phe Thr Lys Gly Tyr Gly Phe Gly Leu Arg Gln Ile Lys Ile Trp
            20                  25                  30

Phe Gln Asn Arg Arg Met Lys Trp Lys Lys
        35                  40

<210> SEQ ID NO 21
<211> LENGTH: 36
<212> TYPE: PRT
<213> ORGANISM: Artificial Sequence
<220> FEATURE:
<223> OTHER INFORMATION: Synthetic Peptide

<400> SEQUENCE: 21

Met Ala Val Pro Pro Thr Tyr Ala Asp Leu Gly Lys Ser Ala Arg Asp
1               5                   10                  15

Val Phe Thr Lys Arg Gln Ile Lys Ile Trp Phe Gln Asn Arg Arg Met
            20                  25                  30

Lys Trp Lys Lys
        35

<210> SEQ ID NO 22
<211> LENGTH: 43
<212> TYPE: PRT
<213> ORGANISM: Artificial Sequence
<220> FEATURE:
<223> OTHER INFORMATION: Synthetic Peptide

<400> SEQUENCE: 22

Arg Gln Ile Lys Ile Trp Phe Gln Asn Arg Arg Met Lys Trp Lys Lys
1               5                   10                  15

Ser Trp Thr Trp Glu Lys Lys Leu Glu Thr Ala Val Asn Leu Ala Trp
            20                  25                  30

Thr Ala Gly Asn Ser Asn Lys Trp Thr Trp Lys
        35                  40

<210> SEQ ID NO 23
<211> LENGTH: 283
<212> TYPE: PRT
<213> ORGANISM: Human VDAC1

<400> SEQUENCE: 23

Met Ala Val Pro Pro Thr Tyr Ala Asp Leu Gly Lys Ser Ala Arg Asp
1               5                   10                  15

Val Phe Thr Lys Gly Tyr Gly Phe Gly Leu Ile Lys Leu Asp Leu Lys
```

```
                    20                  25                  30
Thr Lys Ser Glu Asn Gly Leu Glu Phe Thr Ser Ser Gly Ser Ala Asn
                35                  40                  45

Thr Glu Thr Thr Lys Val Thr Gly Ser Leu Glu Thr Lys Tyr Arg Trp
     50                  55                  60

Thr Glu Tyr Gly Leu Thr Phe Thr Glu Lys Trp Asn Thr Asp Asn Thr
 65                  70                  75                  80

Leu Gly Thr Glu Ile Thr Val Glu Asp Gln Leu Ala Arg Gly Leu Lys
                85                  90                  95

Leu Thr Phe Asp Ser Ser Phe Ser Pro Asn Thr Gly Lys Lys Asn Ala
                100                 105                 110

Lys Ile Lys Thr Gly Tyr Lys Arg Glu His Ile Asn Leu Gly Cys Asp
                115                 120                 125

Met Asp Phe Asp Ile Ala Gly Pro Ser Ile Arg Gly Ala Leu Val Leu
        130                 135                 140

Gly Tyr Glu Gly Trp Leu Ala Gly Tyr Gln Met Asn Phe Glu Thr Ala
145                 150                 155                 160

Lys Ser Arg Val Thr Gln Ser Asn Phe Ala Val Gly Tyr Lys Thr Asp
                165                 170                 175

Glu Phe Gln Leu His Thr Asn Val Asn Asp Gly Thr Glu Phe Gly Gly
                180                 185                 190

Ser Ile Tyr Gln Lys Val Asn Lys Lys Leu Glu Thr Ala Val Asn Leu
                195                 200                 205

Ala Trp Thr Ala Gly Asn Ser Asn Thr Arg Phe Gly Ile Ala Ala Lys
        210                 215                 220

Tyr Gln Ile Asp Pro Asp Ala Cys Phe Ser Ala Lys Val Asn Asn Ser
225                 230                 235                 240

Ser Leu Ile Gly Leu Gly Tyr Thr Gln Thr Leu Lys Pro Gly Ile Lys
                245                 250                 255

Leu Thr Leu Ser Ala Leu Leu Asp Gly Lys Asn Val Asn Ala Gly Gly
                260                 265                 270

His Lys Leu Gly Leu Gly Leu Glu Phe Gln Ala
        275                 280

<210> SEQ ID NO 24
<211> LENGTH: 36
<212> TYPE: PRT
<213> ORGANISM: Artificial Sequence
<220> FEATURE:
<223> OTHER INFORMATION: Synthetic Peptide

<400> SEQUENCE: 24

Cys Cys Cys Thr Thr Cys Gly Ala Thr Cys Gly Cys Gly Gly Ala
1               5                   10                  15

Ala Thr Thr Cys Cys Ala Gly Gly Ala Thr Cys Cys Thr Cys Cys Cys
                20                  25                  30

Ala Gly Cys Cys
        35

<210> SEQ ID NO 25
<211> LENGTH: 36
<212> TYPE: PRT
<213> ORGANISM: Artificial Sequence
<220> FEATURE:
<223> OTHER INFORMATION: Synthetic Peptide

<400> SEQUENCE: 25
```

```
Gly Gly Cys Thr Gly Gly Gly Ala Gly Gly Ala Thr Cys Cys Thr Gly
1               5                   10                  15
Gly Ala Ala Thr Thr Cys Cys Gly Gly Cys Gly Ala Thr Cys Gly Ala
            20                  25                  30
Ala Gly Gly Gly
        35
```